US010429352B2

(12) United States Patent
Cetinkaya

(10) Patent No.: US 10,429,352 B2
(45) Date of Patent: Oct. 1, 2019

(54) METHODS AND SYSTEMS FOR IN-AND OUT-OF-DIE MONITORING AND CHARACTERIZATION OF MULTI-COMPONENT TABLETS AND FOR DETECTING AND MONITORING STICTION AND TOOLING MATERIAL MODIFICATIONS ON PUNCH AND DIE SURFACES

(71) Applicant: Cetin Cetinkaya, Potsdam, NY (US)

(72) Inventor: Cetin Cetinkaya, Potsdam, NY (US)

(73) Assignee: Clarkson University, Postday, NY (US)

( * ) Notice: Subject to any disclaimer, the term of this patent is extended or adjusted under 35 U.S.C. 154(b) by 119 days.

(21) Appl. No.: 15/473,869

(22) Filed: Mar. 30, 2017

(65) Prior Publication Data

US 2017/0269038 A1  Sep. 21, 2017

Related U.S. Application Data

(60) Division of application No. 14/149,356, filed on Jan. 7, 2014, now Pat. No. 9,739,753, which is a continuation-in-part of application No. 11/725,963, filed on Mar. 20, 2007, now Pat. No. 8,645,084.

(60) Provisional application No. 60/808,537, filed on May 26, 2006, provisional application No. 60/783,574, filed on Mar. 20, 2006.

(51) Int. Cl.
*G01N 29/12* (2006.01)
*B30B 11/00* (2006.01)

(52) U.S. Cl.
CPC ............ *G01N 29/12* (2013.01); *B30B 11/005* (2013.01)

(58) Field of Classification Search
CPC .............................. G01N 29/12; B30B 11/005
See application file for complete search history.

(56) References Cited

U.S. PATENT DOCUMENTS 4,854,149 A * 8/1989 Porucznik .......... B21D 51/2615
72/352

* cited by examiner

*Primary Examiner* — Toan M Le
(74) *Attorney, Agent, or Firm* — Bond Schoeneck & King, PLLC; George R. McGuire

(57) ABSTRACT

The present invention relates to a methods and systems for monitoring and/or characterizing multi-component tablets and for monitoring punch and die surfaces and, more particularly, to methods and systems for in-die and out-of-die monitoring and/or characterizing multi-component tablets based on acoustic and vibrational spectroscopy and for detecting and monitoring stiction and tooling material modifications on punch and die surfaces during compaction based on acoustic/ultrasonic waves.

5 Claims, 39 Drawing Sheets

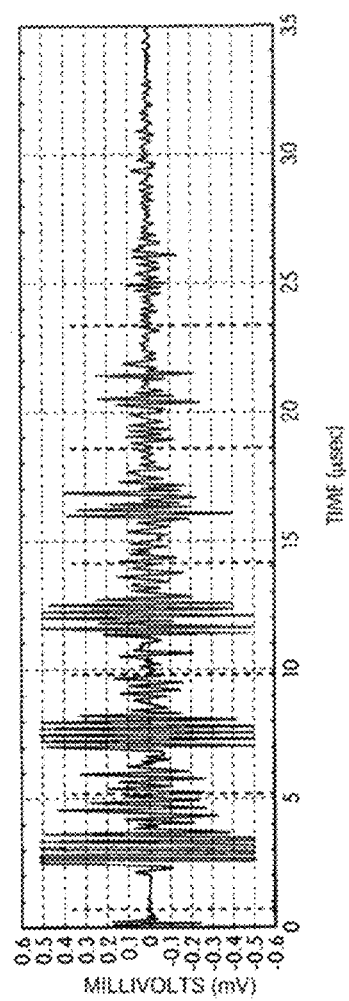

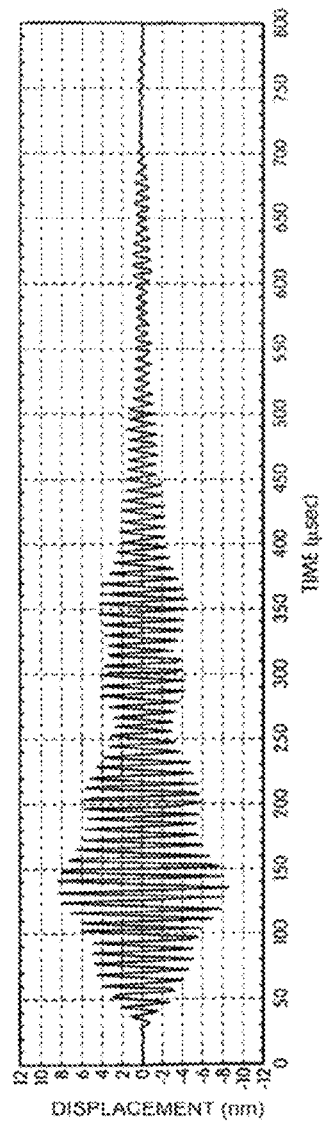

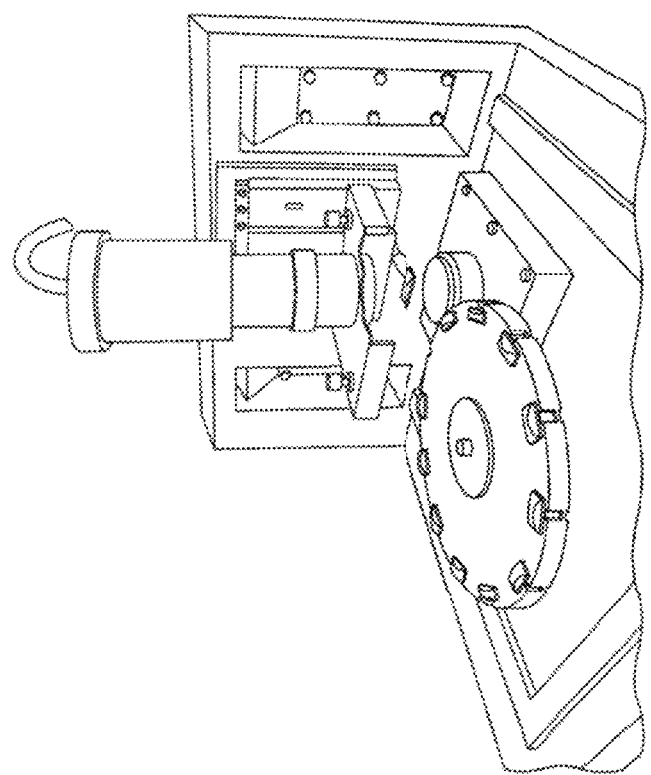

METHODS AND SYSTEMS FOR IN-AND OUT-OF-DIE MONITORING AND CHARACTERIZATION OF MULTI-COMPONENT TABLETS AND FOR DETECTING AND MONITORING STICTION AND TOOLING MATERIAL MODIFICATIONS ON PUNCH AND DIE SURFACES

CROSS REFERENCE TO RELATED APPLICATIONS

This application is a divisional of U.S. Non-Provisional patent application Ser. No. 14/149,356 filed on Jan. 7, 2014 and claims priority to U.S. Non-Provisional patent application Ser. No. 11/725,963 filed on Mar. 20, 2007, which claims priority to Provisional Patent Application Ser. No. 60/783,574 filed on Mar. 20, 2006 entitled Method for Monitoring and Characterization of Solid Dosage during Compaction and Provisional Patent Application Ser. No. 60/808,537 filed on May 26, 2006 entitled Method for Non-contact Mechanical Property Characterization and Monitoring of Drug Tablets, which are incorporated herein by reference in their respective entireties.

FIELD OF INVENTION

The present invention relates to a methods and systems for monitoring and/or characterizing multi-component tablets and for monitoring punch and die surfaces and, more particularly, to methods and systems for in-die and out-of-die monitoring and/or characterizing multi-component tablets based on acoustic and vibrational spectroscopy and for detecting and monitoring stiction and tooling material modifications on punch and die surfaces during compaction based on acoustic/ultrasonic waves.

BACKGROUND OF INVENTION

In order to promote comprehensive quality assurance monitoring in the pharmaceutical industry the Food and Drug Administration (FDA) has initiated a program entitled the Process Analytical Technology (PAT) which is often defined as "a system for designing, analyzing, and controlling manufacturing through timely measurements (i.e. during processing) of critical quality and performance attributes of raw and in process materials, and processes with the goal of ensuring final pharmaceutical product quality." It is important to note that the term analytical in PAT is viewed broadly to include chemical, physical, microbiological, mathematical, and risk analysis conducted in an integrated manner. The approaches detailed in this disclosure are targeted for such monitoring and evaluation tasks.

Physical properties and mechanical integrity of drug tablets often affect their therapeutic functions. This disclosure presents non-contact/non-destructive techniques for determining the mechanical properties of coated tablets, such as Young's moduli, Poisson's ratios and mass densities as well as the thickness of the coating layer using an air-coupled approach is presented. Due to the elevated regulatory and competitive requirements, the demand for measuring and evaluating the mechanical properties of drug tablets has been increasing in the pharmaceuticals industry.

Compaction is a common production method for solid dosage formation from powder and/or granular materials in various industries. Solid dosage (e.g. drug tablets) cores are manufactured by applying pressure to a powder bed to compress the powder into a (porous) coherent/solid form. Compaction represents one of the most important unit operations in the pharmaceuticals industry. Physical and mechanical/elastic properties of the tablets, such as density, hardness and/or mechanical strength as well as geometric features, are determined during the compaction process. These properties can play crucial roles in pharmaceutical effectiveness and functions of a tablet such as tablet integrity and drug availability. The uniaxial compaction of a pharmaceutical powder results in an anisotropic and heterogeneous tablet with variations in such properties as density, porosity and mechanical strength throughout the tablet. During the compaction, various types of defect types can be created in tablets during compaction process, such as capping, chipping, cracking, and splitting. While many of these defect types can be easily identifiable through visual inspections of their exteriors, the defects formed in the interior of a tablet such as cracks are considerably more difficult to detect. Such invisible defects can result in functionally compromised tablets.

Some of the commonly defects occurred during compaction operation are as follows.

Capping is the term used, when the upper or lower segment of the tablet separates horizontally, either partially or completely from the main body of a tablet and comes off as a cap, during ejection from the tablet press, or during subsequent handling. Lamination is the separation of a tablet into two or more distinct horizontal layers. The main reason for these types of defect is that the air-entrapment in a compact during compression, and subsequent expansion of tablet on ejection of a tablet from a die causes capping and lamination.

Chipping is defined as the breaking of tablet edges, while the tablet leaves the press or during subsequent handling and coating operations. The major reasons of chipping include incorrect machine settings and specially mis-set ejection take-off.

Cracking (small, fine cracks) observed on the upper and lower central surface of tablets, or very rarely on the sidewall is often as a result of rapid expansion of tablets, especially when deep concave punches are used. Many mechanical and materials factors such as stress localization and poor adhesion conditions can cause cracks in a tablet core.

Cracking/Splitting is defect in which the film either cracks across the crown of the tablet (cracking) or splits around the edges of the tablet (Splitting) under internal stresses in the film that exceeds tensile strength of the film. Sticking refers to the tablet material adhering to the die wall. Filming is a slow form of sticking and is largely due to excess moisture in the granulation (due to improperly dried or improperly lubricated granules).

Picking is the term used when a small amount of material from a tablet is sticking to and being removed off from the tablet-surface by a punch face. Picking defect is more prevalent on the upper punch faces than on the lower ones. If tablets are repeatedly manufactured in this station of tooling, the size of the defect becomes larger the more and more material getting added to the already stuck material on the punch face. Picking is of particular concern when punch tips have engraving or embossing letters, as well as the granular material is improperly dried.

When the tablets adhere, seize or tear in the die, a film is formed in the die and ejection of tablet is hindered. This type of defect is termed as binding. With excessive binding, the tablet sides are cracked and it may crumble apart. Binding is usually due to excessive amount of moisture in granules, lack of lubrication and/or use of worn dies.

In recent years, deformation and compaction characteristics of the tableting materials have been intensely studied. See: Fell J. T., Newton, J. M., 1968, Tensile strength of lactose tablets, The Journal of Pharmacy and Pharmacology, 20, 657-659; Fell J. T., Newton, J. M., 1970, The prediction of the tensile strength of tablets, The Journal of Pharmacy and Pharmacology, 22, 247; Hancock, B. C., Colvin, J. T., Mullarney, M. P. Zinchuk, A. V., 2003, The relative densities of pharmaceutical powders, blends, dry granulations, and immediate-release tablets, Pharmaceutical Technology, 27, 64-80 (Payne et al.); R. S., Roberts R. J., Rowe R. C., McPartlin M., Bashall A., 1996, The mechanical properties of two forms of primidone predicted from their crystal structures, International Journal of Pharmaceutics, 145, 165-173 (Robert et al.); Roberts R. J., Payne R. S., Rowe R. C., 2000, Mechanical property predictions for polymorphs of sulphathiazole and carbamazepine, European Journal of Pharmaceutical Sciences, 9, 277-283; Roberts R. J., Rowe R. C., 1987, The Young's modulus of pharmaceutical materials, International Journal of Pharmaceutics, 37, 15-18; Bassam F., York P., Rowe R. C., Roberts R. J., 1990, Young's modulus of powders used as pharmaceutical excipients, International Journal of Pharmaceutics, 64, 55-60; and Rigdway K., Aulton M. E., 1970, The surface hardness of tablets, Journal of Pharmacy and Pharmacology, 22, 70-78, all hereby incorporated herein by reference.

One main objective has been to determine the powder behavior during compaction and to understand the effect of the processing of tableting stages on the compaction properties of final products. Even though physical-mechanical properties of tablets are known to influence the tablet chemical and physical stability, accuracy of dosage and appropriate self life, few studies have focused on properties such as the Young's modulus, tensile strength and Poisson's ratio of the core and coating layer of the tablets. See Felton L. A., Shah N. H., Zhang G., Infeld M. H., Malick A. W., McGinity J. W., 1996, Physical-mechanical properties of film-coated soft gelatin capsules, International Journal of Pharmaceutics, 127, 203-211 (Felton et al.); and Stanley P., Rowe R. C. and Newton J. M., 1981, Theoretical considerations of the influence of polymer film coatings on the mechanical strength of tablets. Journal of Pharmacy and Pharmacology, 33, 557-560 both hereby incorporated by reference.

Fell and Newton as cited above investigated the tensile strength of the tablets by diametrical compression tests. Felton et al. as cited above studied the physical-mechanical properties of film-coated tablets including tensile strength, Young's modulus and tensile roughness using a diametrical compression test. In a diametrical compression test as discussed by Fell and Newton, the tablet is placed between two jaws and crushed. The force applied to break the tablet is recorded along with the outer dimensions of the tablet and tensile strength is calculated. The determination of the tensile strength of individual tablet components is used to predict the resultant tensile strength of tablet as a whole.

An important objective of the physical-mechanical property of coating films is to predict the stability and release property of film-coated dosage forms. Tablet coating has been effectively used to protect the dosage form from its environment, to control the release of active ingredients in the body, and to prevent interactions between ingredients. Additionally, tablet coating has improved the mechanical strength of the dosage form to preserve tablet integrity during packaging and shipping. Several researchers have focused on tensile strength and the elastic modulus of free-standing films prepared via aqueous coating technology. See Gutierrez-Rocca J. C. and McGinity J. W., 1993, Influence of aging on the physical-mechanical properties of acrylic resin films cast from aqueous dispersions and organic solutions, Drug Development and Industrial Pharmacy, 19, 315-332; Gutierrez-Rocca J. C. and McGinity J. W., 1994, Influence of water soluble and insoluble plasticizers on the physical and mechanical properties of acrylic resin copolymers, International Journal of Pharmaceutics, 103, 293-301; and Obara S. and McGinity J. W., 1994; Properties of free films prepared from aqueous polymers by a spraying technique; Pharmaceutical Research, 11, 1562-1567, all hereby incorporated by reference. The Obara and McGinty study cited above compared the properties of cast films to sprayed films. It has been reported that the mechanical property variation of the sprayed films are lower and their tensile strength are higher than those of the cast films.

Payne et al. and Roberts et al. (both cited above) developed a molecular modeling approach for predicting Young's moduli of compacts and tableting materials. A mechanical model of crystal structure was used to determine the crystal lattice energy, from which Young's moduli of a series of compacts prepared from aspirin and polymorphs of primidone, carbamazepine and sulphathiazole could be extracted. However, reportedly it is difficult to obtain the bulk elastic properties of tablet materials from the first principles based on molecular dynamic simulations.

Acoustic emission (AE) techniques during processes have been widely utilized in the pharmaceuticals industry due to its cost effective and noninvasive nature for monitoring granular materials to predict their flow, particle size and compaction properties of the final granules. Wong et al. differentiate the deformation mechanisms of single crystals of lactose monohydrate and anhydrous lactose by acoustic emission. It is reported that acoustic emission techniques can be employed to predict the compaction properties and brittleness of tableting materials if the bulk material is characterized by a single-crystal. See: Wong D. Y. T., Waring M. J., Wright P. and Aulton M. E., 1991, Elucidation of the compressive deformation behavior of $\alpha$-lactose monohydrate and anhydrous $\alpha$-lactose single crystals by mechanical strength and acoustic emission analyses, International Journal of Pharmaceutics, 72, 233-241 (Wong et al.) hereby incorporated by reference.

Waring et al. and Hakanen and Laine investigated the acoustic emission of lactose, sodium chloride, microcrystalline cellulose and paracetamol during compression using an acoustic transducer coupled to a portable activity meter. See Hakanen A., Laine E., 1993, Acoustic emission during powder compaction and its frequency spectral analysis, Drug Development and Industrial Pharmacy, 19, 2539-2560 (Waring et al.); and Hakanen A., Laine E., 1995, Acoustic Characterization of a micro-crystalline cellulose powder during and after its compression, Drug Development and Industrial Pharmacy, 21, 1573-1582, hereby incorporated by reference. By computationally analyzing the acoustic peaks related with the particle compression and decompression, it is concluded that the deformation mechanism and capping tendency can be predicted (See Hakanen and Laine cited above). Measuring acoustic emission from process chambers is also used for the identification of various phenomena that can occur during powder compaction of pharmaceutical products, such as granular rearrangement, fragmentation, visco-plastic deformation of grains or granules. See Serris E., Camby-Perier L., Thomas G., Desfontaines M., Fantozzi G., 2002. Acoustic Emission of Pharmaceutical Powders during Compaction, Powder Technology, 128, 2-3, 296-299. Acoustic emission is a passive acoustic technique thereby control over the nature of excitation is often limited.

Hardy and Cook reviewed the use of near infrared spectroscopy (NIR), a non-destructive remote technique as being primarily used for monitoring and predicting the end-points of granulation and drying operations. See Hardy I. J. and Cook W. G., 2003, Predictive and correlative techniques for the design, optimization and manufacture of solid dosage forms, Journal of Pharmacy and Pharmacology, 55 (1), 3-18 hereby incorporated by reference. The potential use of NIR has also been studied to predict tablet hardness. See Morisseau K. M., Rhodes C. T., 1997, Near-infrared spectroscopy as a nondestructive alternative to conventional tablet hardness testing, Pharmaceutical Research, 14 (1), 108-111; Kirsch J. D., Drennen J. K., 1999, Nondestructive tablet hardness testing by near-infrared spectroscopy: a new and robust spectral best-fit algorithm. Journal of Pharmaceutical and Biomedical Analysis, 19 (3-4), 351-362; Chen Y. X., Thosar S. S., Forbess R. A., Kemper M. S., Rubinovitz R. L., Shukla A. J., 2001, Prediction of drug content and hardness of intact tablets using artificial neural network and near-infrared spectroscopy, Drug Development and Industrial Pharmacy, 27 (7), 623-631;

Donoso M., Kildsig D. O., Ghaly E. S., 2003, Prediction of tablet hardness and porosity using near-infrared diffuse reflectance spectroscopy as a nondestructive method, Pharmaceutical Development and Technology, 8 (4), 357-366; Blanco M., Alcala M., 2006, Content uniformity and tablet hardness testing of intact pharmaceutical tablets by near infrared spectroscopy—A contribution to process analytical technologies, Analytica Chimica Acta, 557 (1-2): 353-359; and Otsuka M., Yamane I., 2006, Prediction of tablet hardness based on near infrared spectra of raw mixed powders by chemometrics, Journal of Pharmaceutical Sciences, 95, 1425-1433; all hereby incorporated by reference. However, its sensitive calibration and validation requirements for tablet hardness models remain a challenge since it is known that a slight variation in spectral peaks could invalidate a model.

Many solid pharmaceutical dosage mediums are produced with coatings, ideally the tablet should release the material gradually and the drug should be available for digestion beyond the stomach. Tablet coats serve a wide range of purposes, such as to control release of active ingredients in the body, to avoid irritation of oesophagus and stomach, and to protect the stomach from high concentrations of active ingredients, to improve drug effectiveness and stability and to regulate and/or extend dosing interval. In addition coats extend shelf life by protecting the ingredients from degradation, and to enhance the drug stability; that is to protect the drug from moisture, environmental gases, temperature variations and light, to provide a barrier to unpleasant taste or odor, and to improve appearance and acceptability as well as product identity (Cetinkaya et al., 2006; Mathiowitz, 1999). Coatings that form a controlling barrier to the release of the active ingredient and impart a sustained release of the drug are valuable delivery systems that provide convenience as well as patient compliance. Especially this is true for functional coatings such as an enteric coating which is designed to protect the tablet from the acidic environment of the stomach, resulting in drug release in the higher pH environment of the small intestine. Non-uniformity and/or surface or sub-surface defects of the tablet coating can compromise the desired dose delivery and bioavailability of the drug tablet as well as some other functions. Therefore, evaluating the properties of pharmaceutical coatings such as thickness and uniformity is important for demonstrating adequate process controls and quality and for ensuring optimal performance of the final product. As discussed above, in relation to quality and assurance, the Food and Drug Administration (FDA) has initiated a program entitled the Process Analytical Technology (PAT) to address various aspects of manufacturing problems in the pharmaceuticals industry. The PAT initiative is intended to improve consistency and predictability of drug action by improving quality and uniformity of pharmaceutical materials (Hussain et al., 2004).

In the pharmaceuticals industry, various techniques have been employed in coating thickness measurements such as ultrasonic measurements (Akseli et al., 2007), laser induced breakdown spectroscopy (LIES) (Mowery et al., 2002), x-ray fluorescence method (Behncke, 1984), short pulsed of electromagnetic radiation (e.g. TeraHertz pulsed spectroscopy) (Fitzgerald et al., 2005), scanning thermal microscopy and Fourier transform infrared (FTIR) spectroscopy (Felton, 2003). In contact pulse-echo acoustic measurements, short ultrasonic pulses are generated by a piezoelectric transducer to transmit through the tablet. The ultrasonic pulse is reflected from the back side of the tablet and returned to the measurement surface via the shortest possible path. The reflected waveforms are captured by the same transducer and digitized in the oscilloscope. Measuring the displacement of the first back-wall echo from the start of the transmission peak, the longitudinal velocity of sound can be computed (Akseli et al., 2007). The thickness can then be calculated from the calibration of the time base. Throughout these measurements, coupling medium (water, grease, oil, and couplant gel) is required for facilitating the transmission of ultrasonic energy from the transducer into the test specimen.

Short pulsed of electromagnetic radiation and its reflections from interfaces (e.g. TeraHertz pulsed spectroscopy) is used for the analysis of coating thickness of tablets however due to its high cost it is difficult to use this technique in practice. Scanning thermal microscopy, laser induced breakdown spectroscopy (LIES), x-ray fluorescence method and Fourier transform infrared (FTIR) spectroscopy are either expensive or unavailable for rapid online measurements for coating thicknesses of drug tablets. The proposed technique has potential to fulfill a major need in the analysis of drug delivery mechanisms.

Other relevant non-contact techniques for mechanical property determination adopted in various industrial applications include: (i) EMAT (Electro-Magnetic Acoustic Transducer)-based systems, (ii) optical methods, (iii) spectroscopy-based approaches (IR, near-IR, Raman scattering, Plasmon resonance). Nondestructive testing technologies based on EMATs are inapplicable to the determination of mechanical properties of tablets since tablet materials are typically not electrically conductive. Optical methods are often limited to surface, or near-surface properties, and are often irrelevant in sub-surface mechanical property analysis since, in general, drug tablets and coating layers are opaque in the visible and non-visible ranges. In tablet integrity applications, optical techniques are considered indirect methods for mechanical property monitoring and evaluation. For several years, spectroscopic techniques have been used in monitoring various process parameters such as moisture (water and/or alcohol levels) and blending properties of powders. In these measurements, surface properties are sufficient but the penetration of the electromagnetic waves inside the tablet is typically not required and/or not possible. There is no general method to predict the Young's modulus and Poisson's ratios of the core and coating layer of a tablet from the properties of its constituent components even if exact process steps are known. Non-contact acoustic techniques, detailed in this disclosure, have certain advantages in testing and evaluating the mechanical integrity of the core and the coating layer of drug tablets because of the ability for acoustic waves to penetrate the tablet surface and to vibrate entire tablet structures.

Background of Invention Section Disclaimer: To the extent that specific patents/publications/products are discussed above in this Background of Invention Section or elsewhere in this Application, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Background of Invention Section and/or throughout the application, the descriptions/disclosures of which are all hereby incorporated by reference into this document in their respective entirety(ies).

SUMMARY OF INVENTION

A first method of detecting, monitoring or characterizing a drug tablet during compaction includes: forming a tablet from a powder core in a compactor; transmitting acoustic waves into the powder core while the tablet is being formed; receiving acoustic waves from the powder core while the tablet is being formed; measuring data received from the received acoustic waves; calculating the data; and presenting the data. The acoustic waves are generated and received by transducers embedded in die and punches of the compactor. The instrumentation and signal processing are used for the measuring, calculating and presenting the data. The instrumentation includes a pulser/receiver unit, a digitizing oscilloscope, a computer and a computer program product. The computer program product is a computer usable medium having computer readable program code means embodied in the medium for detecting, monitoring or characterizing a drug tablet during compaction. The detecting, monitoring or characterizing includes transmitting acoustic waves into the powder core while the tablet is being formed; receiving acoustic waves from the powder core while the tablet is being formed; measuring data received from the received acoustic waves; calculating the data; and presenting the data.

The apparatus for detecting, monitoring or characterizing a drug tablet during compaction includes a compactor having a plurality of punches and die; a means for forming a tablet from a powder core; a plurality of transducers for transmitting acoustic waves into the powder core while the tablet is being formed; a plurality of transducers for receiving acoustic waves from the powder core while the tablet is being formed; instrumentation coupled to the transducers measuring, calculating and presenting the data. The transducers for transmitting acoustic signal waves to the powder core and the transducers for receiving acoustic waves from the powder core may be single transducer performing both functions.

Subsequent production decisions (e.g. rejection or continuation of the tablet in the manufacturing process) on the tablet can be made based on the processing of the acoustic signals. The main advantage of the invention is that it provides early warning on the mechanical and geometric state of a tablet during compaction to the operator before a number of other processing operations are applied.

A second method determines the mechanical characteristics and coating thickness of a tablet by exciting the tablet with an acoustic field. This followed with acquiring reflected signals from the tablet and digitizing the reflected signals. The mechanical characteristics are extracted from the digitized signals having resonance frequencies within a certain bandwidth. The exciting of the tablet includes vibrating the tablet. The acquiring of reflected signals includes detecting a shift of a reflected laser beam with an interferometer. The digitizing of the reflected signal is performed by an oscilloscope or by a sampling board. The extracting of the mechanical characteristics from the digitized signals having resonance frequencies within a certain bandwidth is achieved using an iterative process. The iterative process is performed by a computer using a computer program product. The mechanical characteristics being measured include Young's modulus, Poisson's ratios, material mass densities and tablet coating thickness.

The computer program product is a computer usable medium having computer readable program code means embodied in the medium for determining the mechanical characteristics and coating thickness. Determining the mechanical characteristics and coating thickness includes exciting the tablet with an acoustic field; acquiring reflected signals from the tablet; digitizing the reflected signals; and extracting mechanical characteristics and coating thickness from the resonance frequencies within a certain bandwidth using an iterative process.

The apparatus for non-contact mechanical property characterization of drug tablets includes: a vacuum wand; an air coupled transducer; an inferometer; a vacuum control unit; pulse generating device; and measurement and calculation instrumentation. The vacuum control unit and vacuum wand retrieves and supports the tablets to be characterized. The air coupled transducer excites the tablets with acoustical waves. The inferometer measures a vibrational response from the excited tablets in a non-contact manner. The instrumentation digitizes and performs an iterative calculation of the vibrational responses to determine the mechanical characteristics of the tablet. The instrumentation further comprises a computer and a computer program product.

Embodiments of the present invention can also include a method and system for in-die and out-of-die monitoring and/or characterizing multi-component tablets (i.e., drycoated tablets, tablet-in-tablet solid dosage, bilayer tablets, tri-layer tablets, osmotic tablets, and so on, as should be understood by those of skill in the art) based on acoustic and vibrational spectroscopy, which are disclosed. Alone with a number of production tools, a compaction press is often employed to make such products by pharmaceutical, nutraceutical, cosmetics, metal and ceramic parts, powder and various other manufacturers for compacting powder/granular material into a solid form, as discussed herein. The dry-coated tablet dosage form (i.e., the tablet-in-tablet design) is a special form of multi-component tablets. Multi-component tablet form typically is a time- and rate-controlled drug delivery device, which consists of a core tablet and an outer layer that is considerably thicker than typical tablet coats, and which completely surrounds the core (inner) tablet. Multi-component tablets format (tablet-in-tablet solid dosage) is adopted in various industries and applications from detergent to pharmaceutical manufacturing. Due to various components and interfaces, such products are more complex and, thus, prone to defects and failure, thus their characterization and testing is of practical interest for product quality improvements and regulatory requirements.

The disclosed approach as set forth in these additional embodiments is for determining the mechanical (physical), interfacial bonding and geometric (size, wall/core thicknesses, core eccentricity, and so on) quality of such multi-component products by acquiring and processing multi-component products' responses to acoustic and vibrational excitations. These mechanical (physical), interfacial, and geometric properties affect the modal structure of the tablet. In the disclosed approach, the variations in the modal response (resonance frequencies and mode shapes) are related to the mechanical (physical), interfacial, and geometric properties using analytical/computational and statistical methods, as disclosed herein. The disclosed method and system can be adopted for inline/online monitoring and characterization of such tablet products as well as post-production quality monitoring and characterization applications when the product is still in the production and/or in the post-production phase.

Embodiments of the present invention can also include a method and system for detecting and monitoring stiction and tooling material modifications on punch and die surfaces during compaction based on acoustic/ultrasonic waves. These embodiments are more fully described in the Detailed Description section below. The material stiction occurs during compaction due to decreased lubricants at the interfaces and/or increased adhesion of powders and other materials used in compaction. Geometric and material modification (e.g. pitting, plastic deformations, etc.) on the punch and die surfaces and bodies occurs because of various reasons such as material fatigue, micro-structure defects, crack formation, cyclic thermal loading, dynamic loading, chemical interactions so on. The disclosed approach is based on the detection of the interactions of acoustic/ultrasonic waves with excess materials on the surfaces of punches and dies and/or geometric/property modifications in the materials of these surfaces. Such detections are used to determine the material addition (due to stiction) to the surfaces of interest and the surface and body modifications in the punch/die materials.

BRIEF DESCRIPTION OF DRAWINGS

The foregoing aspects and many of the attendant advantages of this disclosure will become more readily appreciated as the same become better understood by reference to the following detailed description, when taken in conjunction with the accompanying drawings, wherein:

FIG. 6B illustrates a waveform indicating the time-of-flight and multiple reflections across the tablet cross-section for a second tablet in the pulse-echo mode;

FIG. 8A illustrates the waveform of a first tablet held with the vacuum wand;

FIG. 12A illustrates an example of a potential use of the tablet monitoring evaluation platform including a desktop testing unit and an online monitoring system;

DETAILED DESCRIPTION

This application discloses methods of and devices for non-contact mechanical property determination and coat thicknesses of drug tablets.

A first method described in this disclosure is to detect, monitor and characterize a drug tablet during compaction by means of transmitting and receiving acoustic waves into the powder core, as it is formed in a press (compactor), via transducers embedded in the compactor die and punches. Subsequent production decisions (e.g. rejection or continuation of the tablet in the manufacturing process) on the tablet can be made based on the processing of the acoustic signals. The main advantage of this method is that it provides an early warning on the mechanical and geometric state of a tablet during compaction to the operator before a number of other processing operations are applied.

The objective of this method is to characterize and to monitor the mechanical (physical) and geometric state of the powder core in the die during compaction in a real-time manner. The characterization and detection/monitoring system consists of a plurality of transducers that generate and receive high frequency acoustic wave fields as well as electronic instrumentation and signal processing software.

Figure 1:
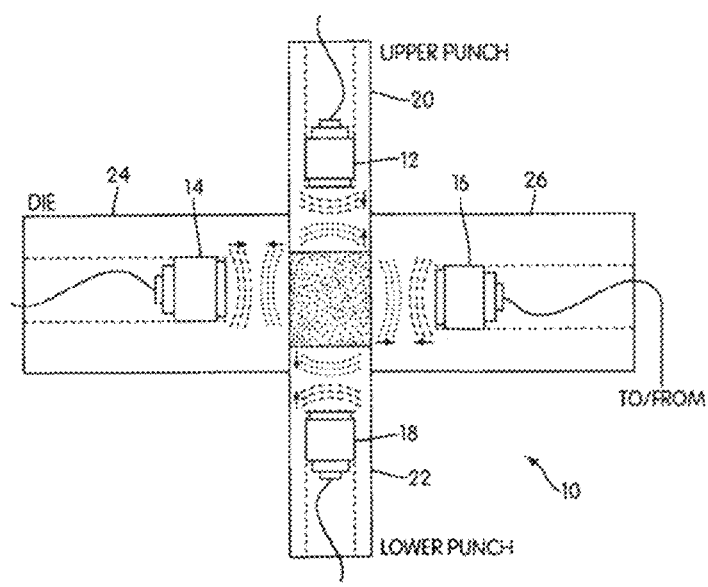
FIG. 1 illustrates four transducers embedded in the upper and lower punches of a compaction device and the die generate and detect acoustic waves through the power core during compaction.
Figure 2:
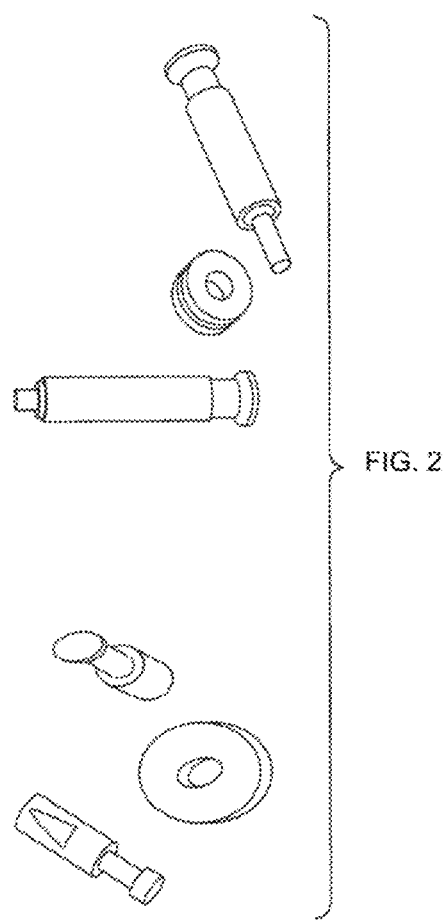
FIG. 2 illustrates examples of typical punches and die sets.

This method detects, monitors and characterizes a drug tablet during compaction by means of transmitting and receiving acoustic waves into the powder core, as it is formed in a press (compactor), via transducers embedded in the compactor die and punches as illustrated in FIG. 1. An image of a typical punches and die set is illustrated in FIG. 2.

FIG. 1 illustrates a compactions device 10 with four transducers embedded 12, 14, 16, and 18 embedded within an upper punch 20, a lower punch 22, a first die 24 and a second die 26. These transducers emit acoustic waves towards the punched tablet and measure its mechanical characteristic. These measurements are coupled to instrumentation calculate and present the results of these measurements. The propagation properties of the powder core in the die during compaction depend on the mechanical properties and their distributions as well as geometric factors (such as delamination zones and cracks). Therefore, by extracting these properties from the transmitted acoustic wave through the powder core, useful information about the material and geometric properties of the powder core can be obtained via instrumentation and signal processing.

Typical instrumentation in such a monitoring and characterization system consists of a pulser/receiver unit, a digitizing oscilloscope (or a sampling board) and a computer (Not shown). Signal processing software is needed to extract the acoustic wave properties of the powder core during compaction such as travel times, reflection and transmission coefficients, and dispersion curves. See references by Morse et al. and Krautkramer et al. cited below. A product of the method is a computer program product or an article of manufacture for use in a computer system having an operating system for use with an apparatus for detecting, monitoring or characterizing a drug tablet during compaction the computer program product having: a computer usable medium having computer readable program code means embodied in the medium for detecting, monitoring or characterizing a drug tablet during compaction, wherein the detecting, monitoring or characterizing includes transmitting acoustic waves into the powder core while the tablet is being formed; receiving acoustic waves from the powder core while the tablet is being formed; measuring data received from the received acoustic waves; calculating the data; and presenting the data.

Typical dwell times of the tablets in the die is on the order of a few milliseconds (ms) (1 ms=10-3 second). For instance, the specified minimum and maximum dwell times for a Presster compaction simulator (Metropolitan Computing Corporation, NJ) are listed as 5.8 ms and 230 ms in the specification list for the Presster compaction simulator.

The travel time of an acoustic field in a tablet with typical dimensions (1-10 mm) is on the order of a few microseconds. Pulse repetition rates of pulser/receiver units can be as high as a few 10 s of kHz. In other words, a commercially available pulser receiver unit can generate high frequency pulses with intervals as low as 0.1 ms (at a pulse repetition rate of 10 kHz). The time-scales of these two processes (e.g. ms for the compaction and μs for acoustic wave propagation) clearly indicate that the number of pulses transmitted and received in the powder core can be sufficiently high (on the order of 10) and the compaction process can be monitored via acoustic waves.

A second non-contact method described in this disclosure is to detect, monitor and characterize a drug tablet mechanical characteristics and coating thickness.

Set-Up and Configurations

Figure 3A:
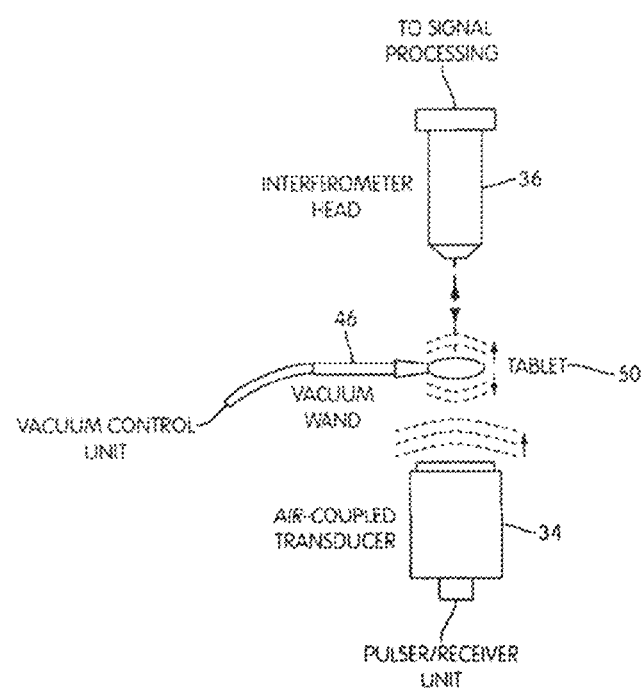
FIG. 3A illustrates schematics of a sample tablet mounting apparatus with the vacuum wand configuration.
Figure 3B:
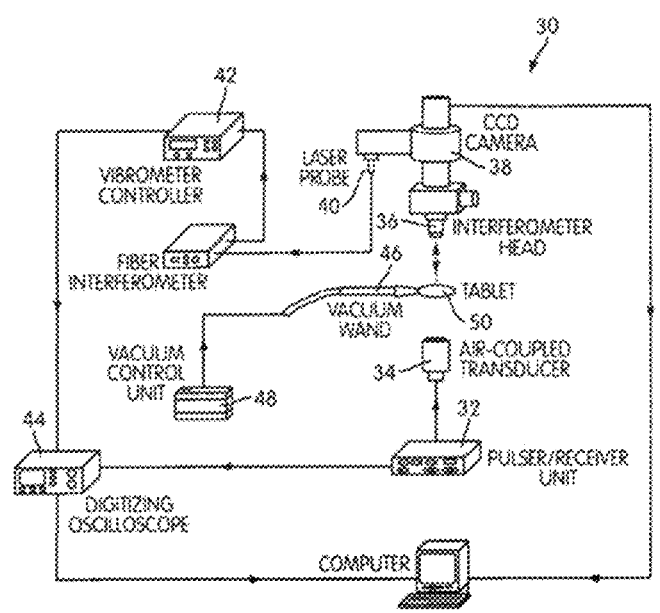
FIG. 3B illustrates schematics of a sample tablet mounting apparatus with the instrumentation diagram of the experimental setup.

An experimental setup utilized for non-contact mechanical property determination of drug tablets is illustrated in FIG. 3 and FIG. 4. FIG. 3A illustrates the tablet measuring portion on a non-contact system 10. A pulser/receiver unit 32 excites an air-coupled transducer 14 with a square pulse. The acoustic field generated on the active surface of the transducer 16 interacts with the tablet 50 and the tablet's vibrational modes are excited. A laser interferometer embedded within a microscope 44 measures the transient out-of-plane motion of a particular point on the surface of the vibrating tablet over a bandwidth of 20 kHz-30 MHz. The interferometer includes a displacement decoder (not shown) with sub-nanometer resolution in the range of ±75 nm The diameter of the interferometric laser beam is specified as small as a few micrometers so that high resolution scans are possible. The setup 30, as shown in FIG. 3B developed for the study incorporated a square pulser/receiver 32, an air-coupled transducer 34, a laser interferometer 36, a CCD camera 38, a laser probe 40 a vibrometer controller 42 and a digitizing oscilloscope 44 (or a sampling board, not shown), as well as a vacuum handling apparatus consisting of a vacuum wand 46 and a vacuum control unit 48 with a suction power of −30 kPa for holding a sample tablet 50.

Figure 4A:
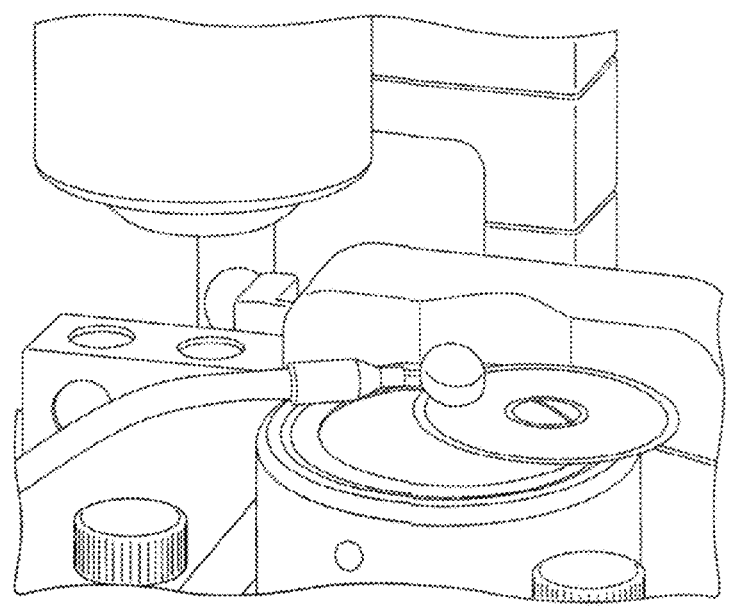
FIG. 4A illustrates an image of the bottom excitation configuration using a 120 kHz transducer with a vacuum wand holding the tablet in place.
Figure 4B:
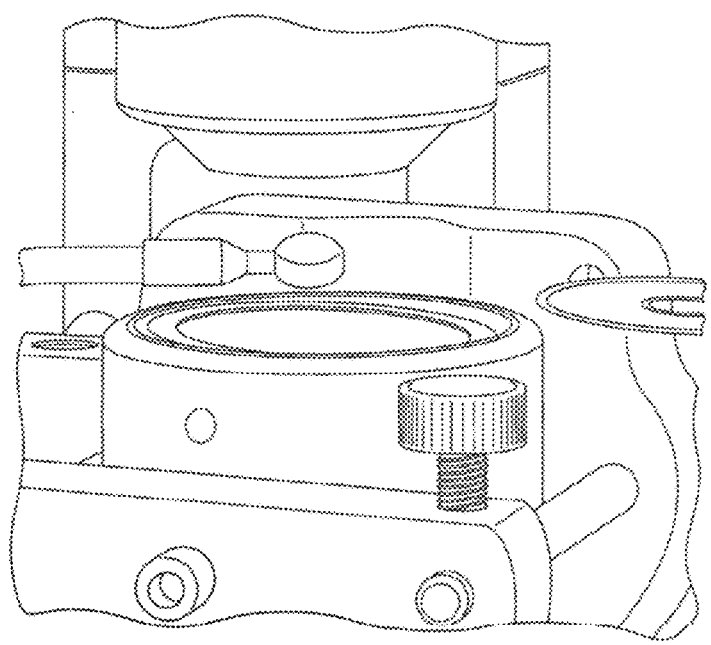
FIG. 4B illustrates another image of the bottom excitation configuration using a 120 kHz transducer with a vacuum wand holding the table in place.
Figure 5A:
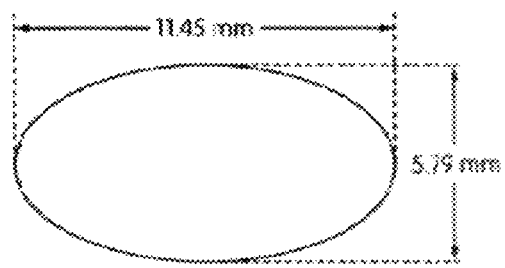
FIG. 5A illustrates the dimensions of a coated tablet with its top view.
Figure 5B:
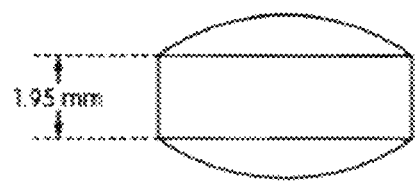
FIG. 5B illustrates the dimensions of a coated tablet with its front view.
Figure 5C:
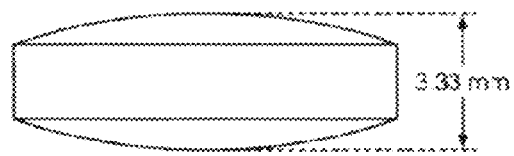
FIG. 5C illustrates the dimensions of a coated tablet with its side view.
Figure 5D:
FIG. 5D illustrates the dimensions of a coated tablet with its side view.

Boundary conditions due to mounting techniques of a tablet have been found to play an important role in the accuracy and sensitivity of transient response measurements. An ideal tablet holding configuration must not interfere with the acoustic field exciting the vibrational motion of the tablet, while holding the tablet firmly with a minimal contact area. In an exemplary embodiment, a vacuum wand is utilized for holding the tablet. The main advantages of the vacuum wand include the firmness of grip, minimal contact surface area with the tablet, and rapidity of the handling apparatus. In experiments of the vacuum wand, a servomotor controlled vacuum control unit is employed to automatically control suction power. As illustrated in FIGS. 4A and 4B, the vacuum wand is used to transport individual tablets from the tablet holding area to the test point.

Procedure for Determining Resonance Frequencies

Sample tablets with the average mass of 200 mg and with the characteristic dimensions of 5.79 mm width, 11.45 mm length, 3.33 mm thickness and a coating thickness of 102.3 µm were employed in the experimental apparatus as shown in FIG. 5. The method equally applies to tablets of different sizes. In determining the resonance frequencies of a sample tablet, the tablet is excited by an acoustic field generated by the air-coupled transducer 34. Since the bandwidth of the transducer overlaps with some of the resonance frequencies of the tablet, the propagating acoustic field generated by the air-coupled transducer excites a number of its vibrational modes. The tablet surface transient responses at measurement points are acquired by the interferometer in a non-contact manner by detecting the shift of a reflected laser beam and are digitized in the oscilloscope. In the vacuum wand mounting apparatus, the air-coupled transducer is placed under the sample tablet at the focal distance of the transducer (See FIG. 4). The focal distance of the transducer used was approximately 2.35 mm. The laser interferometer embedded into the optical microscope is directly focused at a point on the tablet surface through the objective lens of the microscope. The use of the microscope objective allows the laser probe beam to be focused at a spot that can be theoretically reduced to 0.5 µm using a 100× microscope objective. The sample tablet is placed under the objective at a distance of approximately 6.5 mm. The pulser/receiver 12 unit used in this embodiment delivers a 100V square pulse to the transmitting air-coupled transducer and provides a synchronizing pulse to trigger the digital oscilloscope (FIG. 3A). The acquired waveforms are digitized and averaged through the digital oscilloscope 38 and uploaded to a computer 44 in order to determine the vibrational resonance frequencies. Using an iterative computational procedure discussed below, the mechanical properties of the sample tablet core and coating layer can be extracted from a subset of the resonance frequencies in a certain bandwidth.

A computer program product is used with the computer for determining mechanical characteristics and coating thickness of a tablet the computer program product. The computer program product is a computer usable medium having computer readable program code means embodied in the medium for determining the mechanical characteristics and coating thickness and includes exciting the tablet with an acoustic field; acquiring reflected signals from the tablet; digitizing the reflected signals; extracting mechanical characteristics and coating thickness from the resonance frequencies within a certain bandwidth and performing an iterative process to determine the mechanical characteristics and coating thickness of the tablet.

Contact Measurements

Figure 6A:
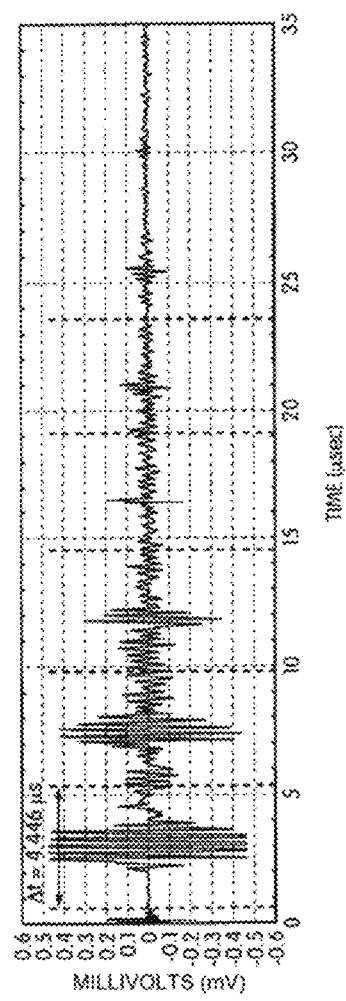
FIG. 6A illustrates a waveform indicating the time-of-flight and multiple reflections across the tablet cross-section for tablet in the pulse-echo mode.

For verification purposes, the Young's modulus of a sample tablet core (□ core) is obtained using contact time-of-flight ultrasonic measurements. The mass densities of the core ($\rho_{core}$) and the coating material ($\rho_{coat}$) of the sample tablet are calculated from direct mass measurements of tablets with various coating thicknesses for known tablet geometry. Property predictions based on contact measurements are used for determining initial mechanical properties and for confirming (non-contact) experimentally obtained mechanical properties. In determining the Young's modulus of the core material ($E_{core}$) of the sample tablet, a direct measurement ultrasonic method (pulse-echo mode) is employed. In this test, short ultrasonic pulses are generated by a piezoelectric transducer with a central frequency to transmit through the tablet. The ultrasonic pulse is reflected from the back side of the tablet and returned to the measurement surface via the shortest possible path. The reflected waveforms are captured by the same transducer and digitized in the oscilloscope, as illustrated in FIG. 6. The thickness of the tablet can easily be measured precisely. The time of flight of an acoustic pulse is a function of its thickness and mass density as well as the tablet's Young's modulus. The longitudinal velocity of sound $c_L$ and Young's modulus of the core material of the tablet are easily computed. Consistent waveforms providing the time-of-flight across the tablet thickness for two different tablets are depicted in FIGS. 4A and 4B. The computed Young's modulus of the core of the sample tablet ($E_{core}$=2628.92 MPa) is included in Table 1. Table 1 outlines the relationships of the various properties used in the iterative computational procedure. $\bar{p}^*$ is the vector of starting mechanical property for the iterative computational procedure. $\bar{p}_1^e$, $\bar{p}_2^e$, $\bar{p}_3^e$ are the extracted mechanical property vectors upon completion of iterative procedure for $\bar{p}^*$ for Tablet 1, Tablet 2, Tablet 3, respectively. $\bar{p}^c$ is the measured and estimated mechanical property vector; $E_{core}$ is calculated from the contact measurements, $\rho_{core}$ and $\rho_{coat}$ are calculated from direct mass measurements. Percentage convergences of initial and experimental mechanical property vectors are shown for three tablets. The estimated mechanical properties ($v_{core}$, $E_{coat}$, $v_{coat}$) for $\bar{p}^c$ are indicated by an asterisk.

TABLE 1

| Mechanical Properties | $\bar{p}^*$ | $\bar{p}_1^e$ | $\bar{p}_2^e$ | $\bar{p}_3^e$ | $\bar{p}^c$ | Convergence (%): $\bar{p}^* - \bar{p}_i^e$ | | |
|---|---|---|---|---|---|---|---|---|
| | | | | | | Tablet 1 | Tablet 2 | Tablet 3 |
| $E_{core}$ (MPa) | 3154.704 | 2648.220 | 2691.112 | 2666.287 | 2628.920† | 19.125 | 17.227 | 18.318 |
| $\rho_{core}$ (kg/m³) | 1591.548 | 1335.763 | 1348.758 | 1329.848 | 1326.290† | 19.207 | 18.001 | 19.679 |
| $v_{core}$ | 0.388 | 0.330 | 0.331 | 0.330 | 0.330* | 17.575 | 17.185 | 17.576 |
| $E_{coat}$ (MPa) | 3600.000 | 3023.150 | 3041.635 | 3038.521 | 3000* | 19.081 | 18.357 | 18.478 |
| $\rho_{coat}$ (kg/m³) | 868.410 | 730.730 | 737.883 | 729.761 | 723.675† | 18.841 | 17.689 | 18.999 |
| $v_{coat}$ | 0.447 | 0.382 | 0.385 | 0.381 | 0.380* | 17.015 | 16.104 | 17.292 |

Finite Element Study for Tablet Spectral Properties

The spectral properties of a tablet are related to its mechanical properties (e.g. Young's moduli ($E_{core}$, $E_{coat}$), Poisson's ratios ($v_{core}$, $v_{coat}$) and material mass densities ($\rho_{core}$, $\rho_{coat}$) of the core and the coating layer) as well as its geometry (e.g. shape and dimensions of the core and the coating layer). Using a finite element algorithm, such as the Lanczos method, the spectral properties of the tablet (e.g. a set of resonance frequencies and corresponding mode shapes) can be obtained provided that the mechanical properties and geometry of the tablet are available. However, the extraction of the tablet mechanical properties from its measured resonance frequencies requires the use of an iterative computational procedure such as Newton's method as well as a method to compute its resonance frequencies.

In the finite element study employed to compute natural frequencies of the tablets, a three-dimensional mesh for the tablet is modeled as homogenous and isotropic elastic solid consisting of a core and a coating layer for numerical predictions of the tablet resonance frequencies. The top, front and side views illustrating outer dimensions and cross-sectional area of the coated sample tablet with a coating thickness of 120.3 μm used in the finite element analysis are depicted in FIG. 3. Four-node linear tetrahedron elements are used in the mesh generation for the coated tablet. The number of elements, number of nodes, degrees of freedom and element size of the meshed coated tablet are 62,635, 14,357, 43,071, and 250 μm, respectively. The Lanczos eigenvalue solver implemented in the commercial software package ABAQUS is employed to obtain the resonance frequencies of the modeled tablet in the frequency range of 40 kHz to 200 kHz for given material properties.

Experimental Resonance Frequency Measurements

Figure 7A:
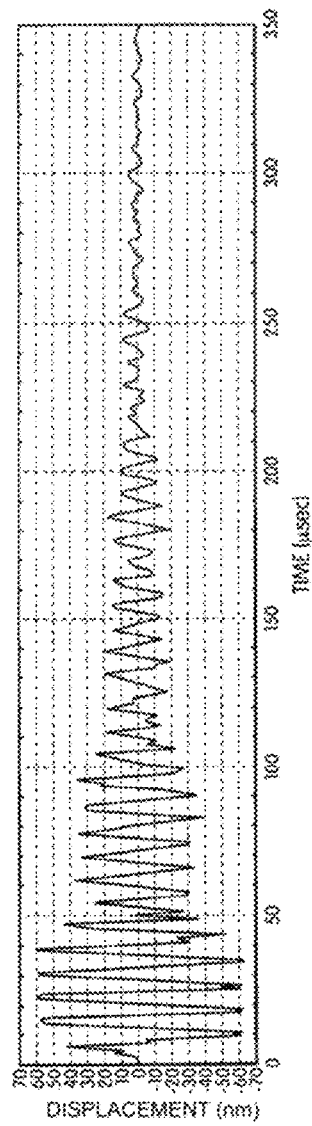
FIG. 7A illustrates the transient displacement on the active surface of the transducer under a square pulse excitation.
Figure 7B:
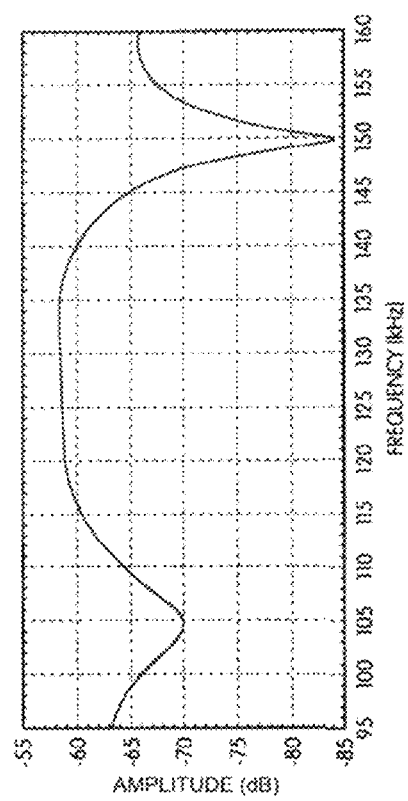
FIG. 7B illustrates the frequency response of a spot on the active surface of the transducer under a square pulse excitation.
Figure 8B:
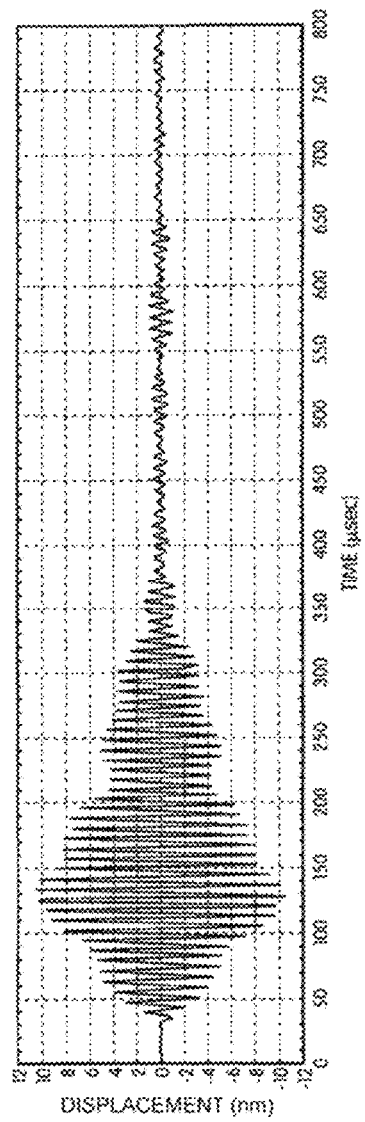
FIG. 8B illustrates the waveforms of a second tablet held with the vacuum wand.
Figure 8C:
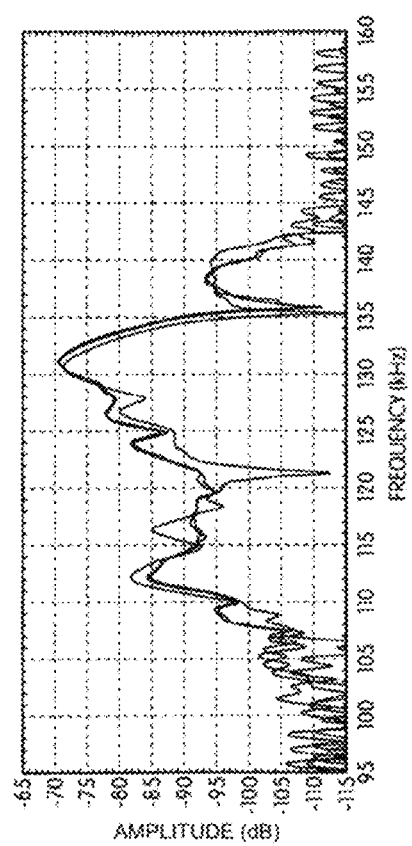
FIG. 8C illustrates a comparison of the frequency responses of the a first tablet in FIG. 8A and a second table in FIG. 8B.

Resonance frequencies of the tablet are obtained by applying the Fast Fourier Transform (FFT) algorithm on the acquired waveforms under air-coupled excitation. The frequency range of the measurements is limited to 105 kHz because 150 kHz due to the bandwidth of the transducer employed in the experiments (See FIG. 7). In the experiments conducted with the vacuum wand, the resonance frequencies and the displacement of the tablet are clearly apparent. The transient surface displacement responses and frequency responses for three sample tablets were measured utilizing the vacuum wand mounting apparatus (FIGS. 8A-8C). Consistent waveforms obtained over an extended time period in the experiments indicate that the air-coupled excitation and the experimental set-up are repeatable and stable.

Sensitivity Analysis for Extracting Tablet Mechanical Properties

In order to extract the mechanical property parameters ($E_{core}$, $E_{coat}$, $v_{core}$, $v_{coat}$, $\rho_{core}$, $\rho_{coat}$) of sample tablets from their resonance frequencies, an iterative procedure based on Newton's method is adopted. From a finite element study, it is observed that shifts in resonance frequencies are nearly linear with the reasonable changes in the mechanical properties, and no intersection of modes is realized within ±20% variation of the initial (estimate) mechanical properties. If modes traverse, the corresponding resonance frequencies will not coincide with their ordered mode shapes and all mode shapes and related resonance frequencies must be verified before continuing the inversion process.

The sensitivity analysis is based on the assumption that there is a well-defined relationship between a change in certain parameters of interest and other parameters of interest. In this type of analysis for mechanical properties, a series of either numerical or actual tests are conducted in which the (mechanical) parameters are altered to approximate these relationships between changes in the (mechanical) parameters, and corresponding changes in the natural frequencies. The result of such a study is sensitivity coefficients that can be used to approximate the assumed relationship. From these sensitivity coefficients, the actual mechanical properties can approximately be extracted within ranges of parameters.

In the mechanical property extraction, a set of initial (estimate) mechanical property vector is chosen $\bar{p}_k^*$ (Table 1) and the corresponding resonance frequency vector $\bar{f}_k^*$ is calculated via the method (Table 2) and each iteration step is denoted by index k. Each mechanical property parameter ($E_{core}$, $\rho_{core}$, $v_{core}$, $E_{coat}$, $\rho_{coat}$, $v_{coat}$) and mode numbers obtained from finite element are denoted by indices i and j, respectively. The thickness of the coat can also be added to this vector when the coat thickness is to be determined. Consistent six modes calculated from finite element (j=1, 2, . . . 6) for $\bar{p}_k^*$ compared to experimentally obtained resonance frequencies $f_{v_1}^e$, $f_{v_2}^e$, $f_{v_3}^e$ (Table 2) for the three sample tablets selected for sensitivity calculations. The i-th component of $\bar{p}_k^*$ is perturbed by a factor of (1+ε) and the six resulting perturbed material property vectors are denoted by $\bar{p}_i$ (i=1, 2, . . . , 6). The finite element model is run for each $\bar{p}_i$ to determine the corresponding six resonance frequency vectors $\bar{f}_i$ and their shifts $\Delta \bar{f}_i = \bar{f}_i - \bar{f}^*$. Using the first term in Taylor's expansion, the sensitivity coefficient vector {s} is approximated for i=1, 2, . . . , 6 as:

$$\Delta \bar{f}_i \cong \{s\}^T \cdot \{\Delta p\} \quad (1)$$

where $$\{\Delta p\} = \{\Delta E_{core} \quad \Delta \rho_{core} \quad \Delta v_{core} \quad \Delta E_{coat} \quad \Delta \rho_{coat} \quad \Delta v_{coat}\}^T$$

$$\{s\} = \left\{ \frac{\partial f_j}{\partial E_{core}} \quad \frac{\partial f_j}{\partial \rho_{core}} \quad \frac{\partial f_j}{\partial v_{core}} \quad \frac{\partial f_j}{\partial E_{coat}} \quad \frac{\partial f_j}{\partial \rho_{coat}} \quad \frac{\partial f_j}{\partial v_{coat}} \right\}^T$$

j is the mode number, $\Delta p = \bar{p}_i - \bar{p}^*$, {s} the sensitivity coefficient vector and $\Delta \bar{f}_i = \bar{f}_i - \bar{f}^*$. After running the finite element model and applying [Eq.1] for i=1, 2, . . . , 6 to calculate the sensitivity coefficients for j=1, 2, . . . , 6, (j=7 is needed if the thickness of the tablet is needed) the sensitivity tangent matrix $[s_\varepsilon]_k$ is constructed for the selected six mode:

$$[S_\varepsilon]_k = \begin{bmatrix} \frac{\partial f_1}{\partial E_{core}} & \frac{\partial f_1}{\partial \rho_{core}} & \frac{\partial f_1}{\partial v_{core}} & \frac{\partial f_1}{\partial E_{coat}} & \frac{\partial f_1}{\partial \rho_{coat}} & \frac{\partial f_1}{\partial v_{coat}} \\ \frac{\partial f_2}{\partial E_{core}} & \frac{\partial f_2}{\partial \rho_{core}} & \frac{\partial f_2}{\partial v_{core}} & \frac{\partial f_2}{\partial E_{coat}} & \frac{\partial f_2}{\partial \rho_{coat}} & \frac{\partial f_2}{\partial v_{coat}} \\ \frac{\partial f_3}{\partial E_{core}} & \frac{\partial f_3}{\partial \rho_{core}} & \frac{\partial f_3}{\partial v_{core}} & \frac{\partial f_3}{\partial E_{coat}} & \frac{\partial f_3}{\partial \rho_{coat}} & \frac{\partial f_3}{\partial v_{coat}} \\ \frac{\partial f_4}{\partial E_{core}} & \frac{\partial f_4}{\partial \rho_{core}} & \frac{\partial f_4}{\partial v_{core}} & \frac{\partial f_4}{\partial E_{coat}} & \frac{\partial f_4}{\partial \rho_{coat}} & \frac{\partial f_4}{\partial v_{coat}} \\ \frac{\partial f_5}{\partial E_{core}} & \frac{\partial f_5}{\partial \rho_{core}} & \frac{\partial f_5}{\partial v_{core}} & \frac{\partial f_5}{\partial E_{coat}} & \frac{\partial f_5}{\partial \rho_{coat}} & \frac{\partial f_5}{\partial v_{coat}} \\ \frac{\partial f_6}{\partial E_{core}} & \frac{\partial f_6}{\partial \rho_{core}} & \frac{\partial f_6}{\partial v_{core}} & \frac{\partial f_6}{\partial E_{coat}} & \frac{\partial f_6}{\partial \rho_{coat}} & \frac{\partial f_6}{\partial v_{coat}} \end{bmatrix}$$

Using $[s_\varepsilon]_k$, the change in mechanical properties vector due to a shift $\{\Delta \bar{f}_k\}$ in the selected set of resonance frequencies can be approximated by $$\{\Delta \bar{p}\}_k = [S_\varepsilon]_k^{-1} \cdot \{\Delta \bar{f}_k\} \quad (2)$$

where $\Delta \bar{f}_k = \bar{f}_\nu^e - \bar{f}^*_k$, and $\{\Delta \bar{p}\}_k$ the change in mechanical properties after the completion of an iteration with the perturbation $\bar{p}_k^e = \bar{p}_k^* + \Delta \bar{p}_k$ (see Table 1 for their numerical values). In this study, a number of iterations are executed to approximate values for $_{core}, _{coat}, _{core}, _{coat}, _{core}$ and $_{coat}$. Once singularity is observed in the tangent matrix $[s_\varepsilon]_k$ or $\{\Delta \bar{p}\}_k$ values converge to zero the iteration loop is terminated. The values of $\bar{p}^*$ used in the last iteration correspond to the experimental mechanical property vector $\bar{p}_k^e$ of the core and coating of the tablet since $\Delta \bar{p}_k \approx 0$ (see Table 1 for the numerical values for the three sample tablets).

Figure 11:
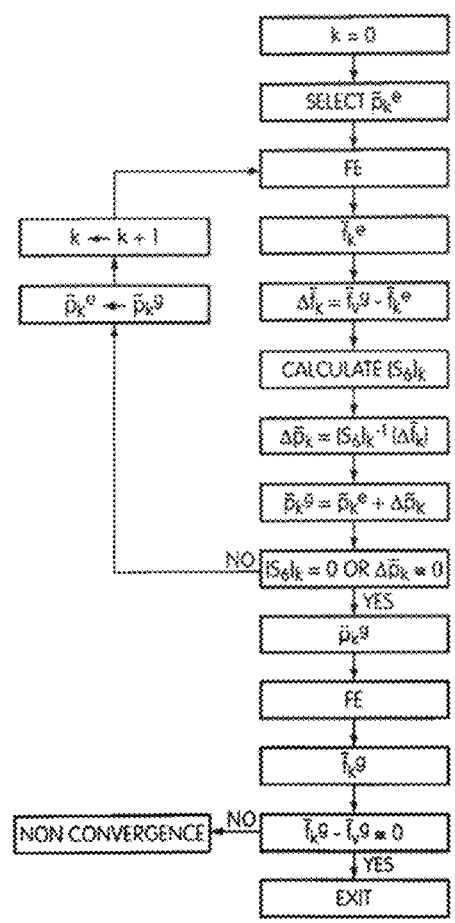
FIG. 11 illustrates a flow chart for the iterative process.

A flow chart for this iterative process is depicted in FIG. 11.

After extracting the mechanical properties for each tablet, the finite element method is employed to determine the corresponding resonance frequencies $\bar{f}_1^e, \bar{f}_2^e, \bar{f}_3^e$ for comparison purposes (see Table 2 for their numerical values). Due to tablet to tablet variations, small differences are detected in mechanical properties and resonance frequencies among three sample tablets. Within ±20% variations of the mechanical properties, changes in resonance frequencies are calculated approximately in the range of ±1.5% as listed in Table 1 and Table 2. The percent error between the experimental resonance frequencies ($\bar{f}_{\nu_1}^e, \bar{f}_{\nu_2}^e, \bar{f}_{\nu_3}^e$) and the finite element resonance frequencies ($\bar{f}_1^e, \bar{f}_2^e, \bar{f}_3^e$) corresponding to extracted mechanical properties is within ±1.5% for three sample tablets (Table 2).

component tablets) showing its structural components (core and coat layers) and interfaces is illustrated. The core tablet 1401 is coated on the sides (side outer layers 1402 and 1402'), top (top outer layer 1404) and bottom (bottom outer layer 1406) layers. The core tablet 1400 has been darkened for visualization purposes. An outer core interface 1408 and a side core interface 1410 are also shown. In more complex dry-coated tablets, complicated core(s) and coat layer(s) can be adopted.

Figure 14:
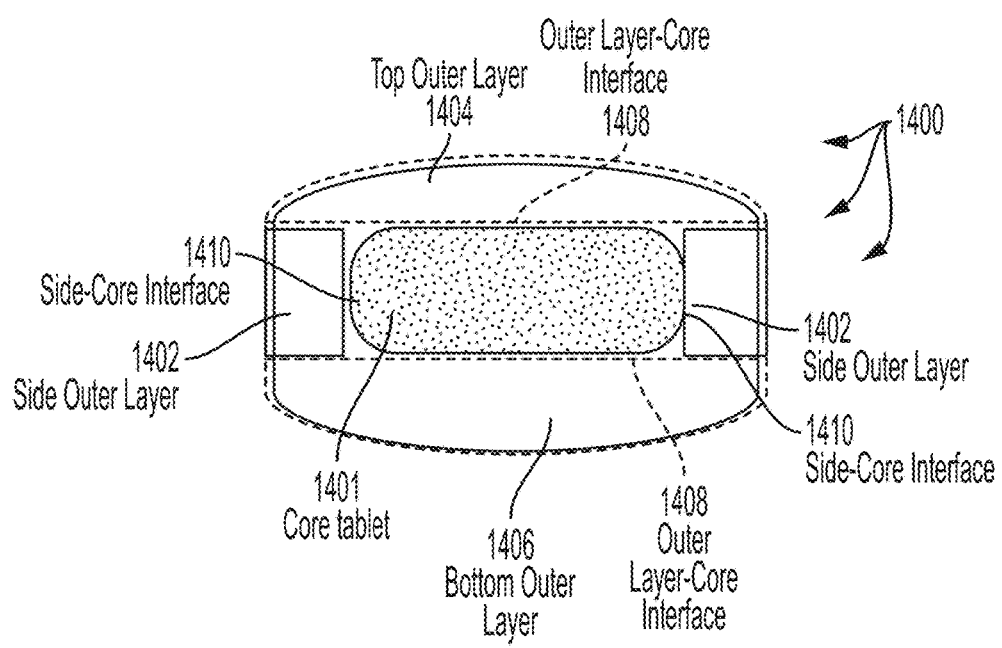
FIG. 14 is a picture of a vertical cross section of a sample dry coated tablet showing its structural components (core and coat layers) and interfaces.
Figure 15A:
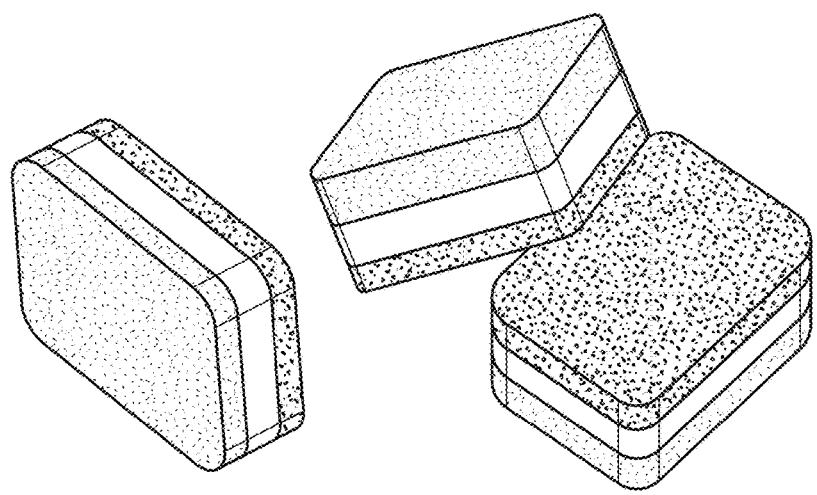
FIG. 15A illustrates a tri-layered tablet design.
Figure 15B:
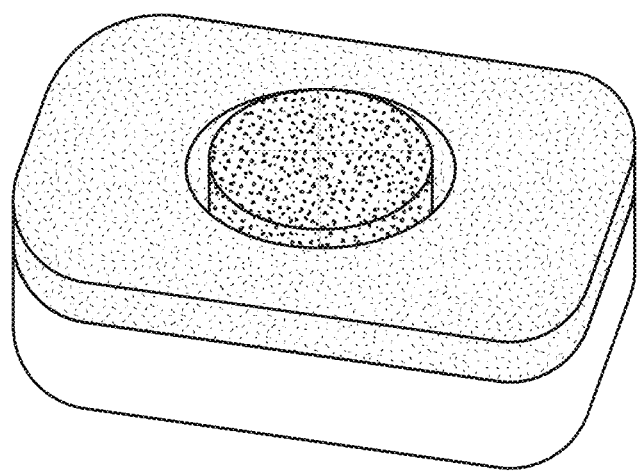
FIG. 15B illustrates a commercial tablet with a complex layered tablet-in-table design.
Figure 15C:
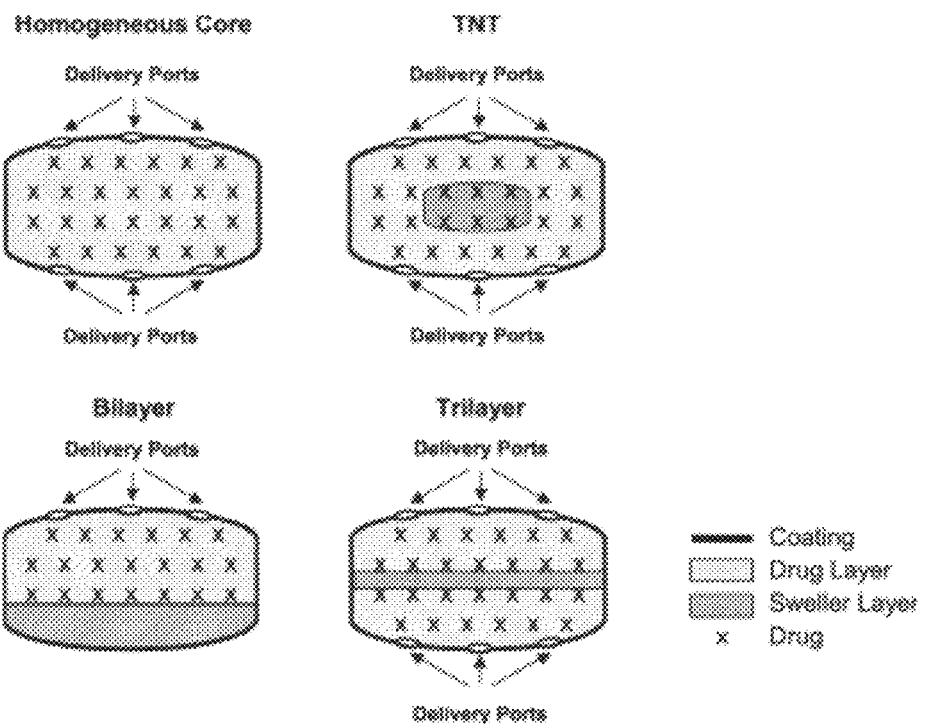
FIG. 15C illustrates a compound tablet design with osmotic pumps and their deliver ports.
Figure 15D:
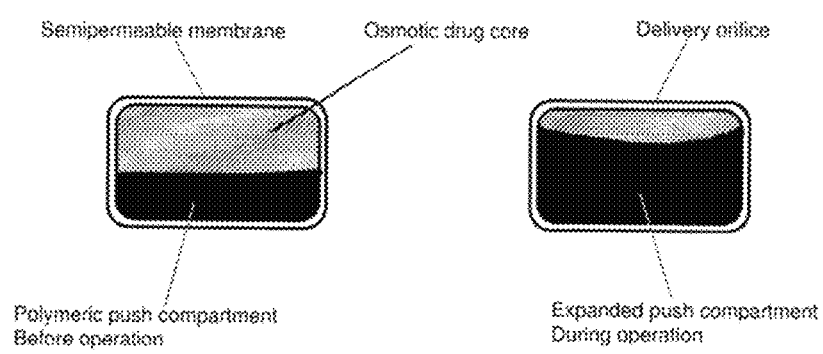
FIG. 15D illustrates an alternative multi-component tablet design.

FIGS. 15A-15C are pictures showing various other types of multi-component tablets (as compared to FIG. 14) from consumer markets and the pharmaceutical industry. FIG. 15A shows a typical tri-layered tablet design; FIG. 15B shows a commercial tablet with complex layered tablet-in-table design; FIG. 15C shows a compound tablet design with osmotic pumps and their delivery ports (orifices); and FIG. 15D shows another multi-component tablet design that can be used as part of an embodiment of the present invention.

Figure 16:
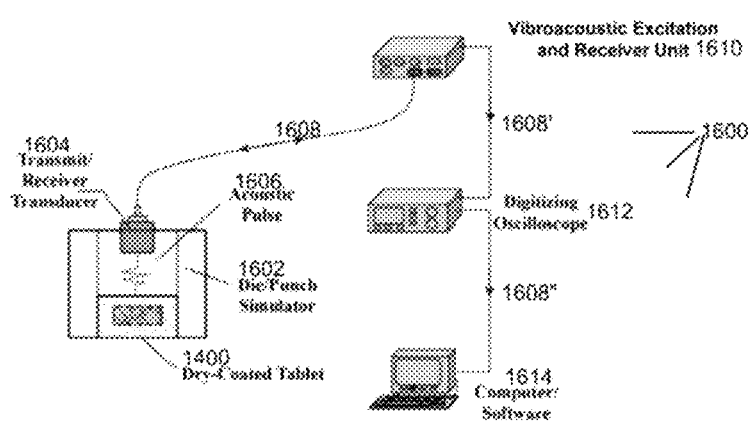
FIG. 16 is a schematic representation of a vibroacoustic excitation and detection system, which is used for in-die monitoring and/or characterizing multi-component tablets in accordance with an embodiment of the present invention.

FIG. 16 is a schematic representation of a vibroacoustic excitation and detection system 1600, which is used for in-die monitoring and/or characterizing multi-component tablets in accordance with an embodiment of the present invention. The vibroacoustic excitation and detection system 1600 can include, but is not limited to, a die/punch simulator 1602 which is configured/structured to contain a dry coated tablet 1400. The transmit/receive transducer 1604 can be embedded in the upper punch portion, as shown in FIG. 16,

TABLE 2

| Modes | $\bar{f}^*$ | $\bar{f}_1^e$ | $\bar{f}_2^e$ | $\bar{f}_3^e$ | Convergence (%): $\bar{f}^* - \bar{f}_i^e$ | | |
|---|---|---|---|---|---|---|---|
| | | | | | Tablet 1 | Tablet 2 | Tablet 3 |
| 8 | 107,331 | 109,135 | 109,338 | 109,675 | −1.653 | −1.835 | −2.137 |
| 9 | 112,089 | 112,175 | 113,391 | 113,750 | −0.076 | −1.148 | −1.460 |
| 11 | 120,891 | 122,621 | 122,869 | 123,235 | −1.411 | −1.609 | −1.902 |
| 13 | 122,150 | 123,863 | 124,118 | 124,492 | −1.383 | −1.585 | −1.881 |
| 14 | 131,641 | 131,646 | 133,017 | 133,362 | −0.004 | −1.034 | −1.290 |
| 15 | 136,547 | 138,418 | 138,776 | 138,157 | −1.352 | −1.606 | −1.165 |

| Modes | $\bar{f}^c$ | $\bar{f}_{\nu_1}^e$ | $\bar{f}_{\nu_2}^e$ | $\bar{f}_{\nu_3}^e$ | Error (%): $\bar{f}^c - \bar{f}_{\nu i}^e$ | | |
|---|---|---|---|---|---|---|---|
| | | | | | Tablet 1 | Tablet 2 | Tablet 3 |
| 8 | 109,085 | 109,137 | 109,412 | 109,210 | −0.047 | −0.298 | −0.114 |
| 9 | 112,149 | 112,181 | 111,910 | 112,150 | −0.028 | 0.213 | −0.00089 |
| 11 | 122,562 | 122,629 | 121,525 | 121,810 | −0.054 | 0.853 | 0.617 |
| 13 | 123,821 | 123,870 | 123,805 | 124,115 | −0.039 | 0.013 | −0.237 |
| 14 | 131,627 | 131,655 | 131,220 | 131,830 | −0.021 | 0.310 | −0.154 |
| 15 | 137,425 | 138,480 | 138,505 | 138,155 | −0.762 | −0.779 | −0.528 |

$\bar{f}^*$ and $\bar{f}^c$ are the finite element resonance frequency vectors corresponding to $\bar{p}^*$ and $\bar{p}^c$, respectively. $\bar{f}_1^e, \bar{f}_2^e, \bar{f}_3^e$ are the finite element resonance frequency vectors, upon completion of sensitivity analysis, corresponding to $\bar{p}_1^e, \bar{p}_2^e, \bar{p}_3^e$ of Tablet 1, Tablet 2, Tablet 3, respectively. $\bar{f}_{\nu_1}^e, \bar{f}_{\nu_2}^e, \bar{f}_{\nu_3}^e$ are the experimental resonance frequency vectors directly measured with the vacuum wand for Tablet 1, Tablet 2, Tablet 3.

Figure 9:
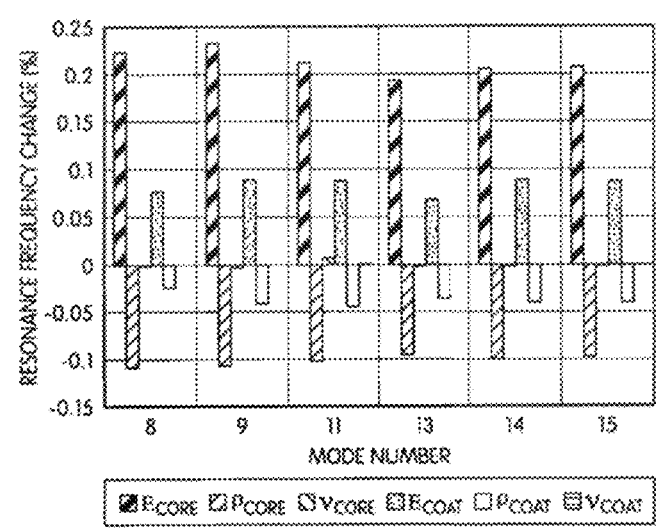
FIG. 9 illustrates the normalized sensitivities of the resonance frequencies of Tablet 1 to the changes in Ecore, ρcore, vcore, Ecoat, ρcoat, and vcoat for the modes 8, 9, 11, 13, 14 and 15.
Figure 10A:
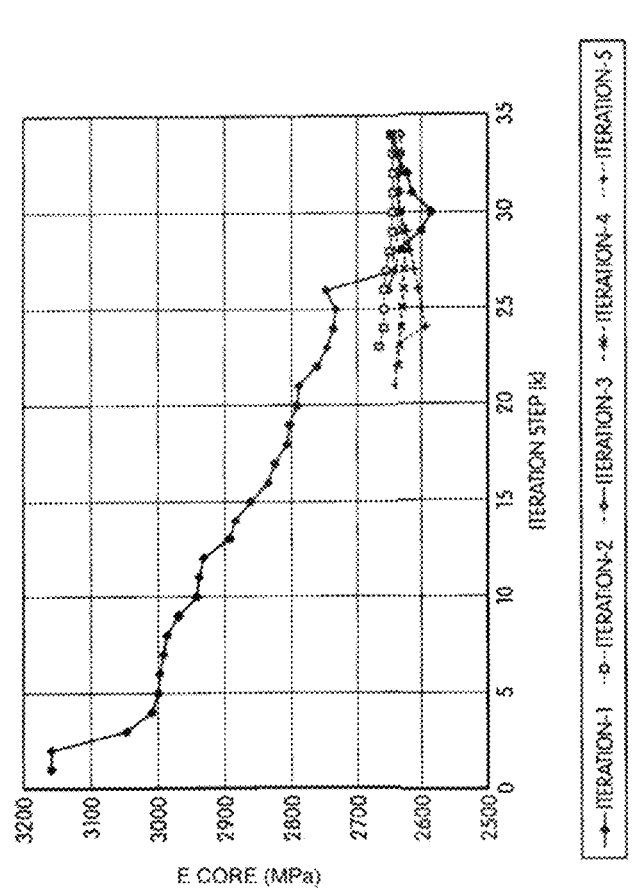
FIG. 10A illustrates the convergence of Ecore (a) of the Tablet 1 during the sensitivity iterations.
Figure 10B:
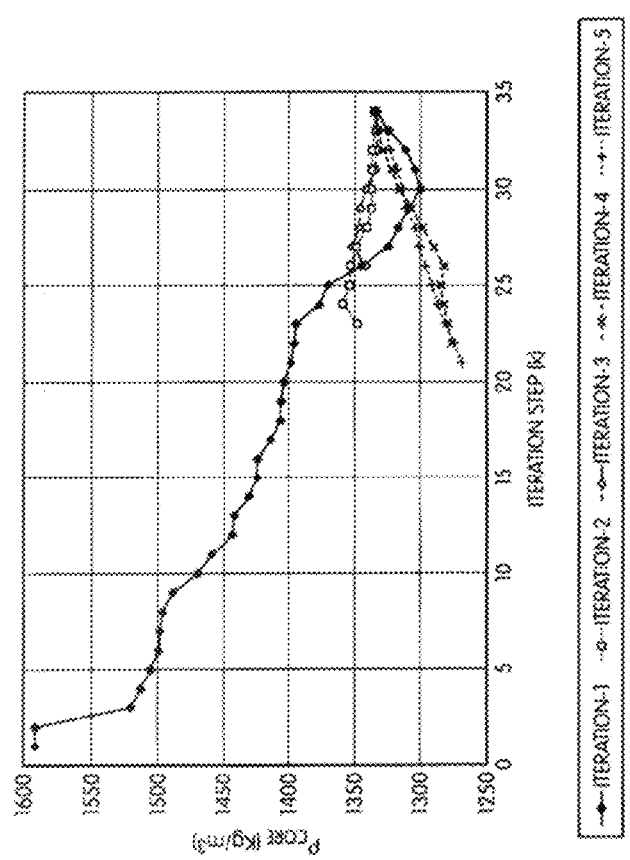
FIG. 10B illustrates the convergence of ρcore (b) of the Tablet 1 during the sensitivity iterations.
Figure 10C:
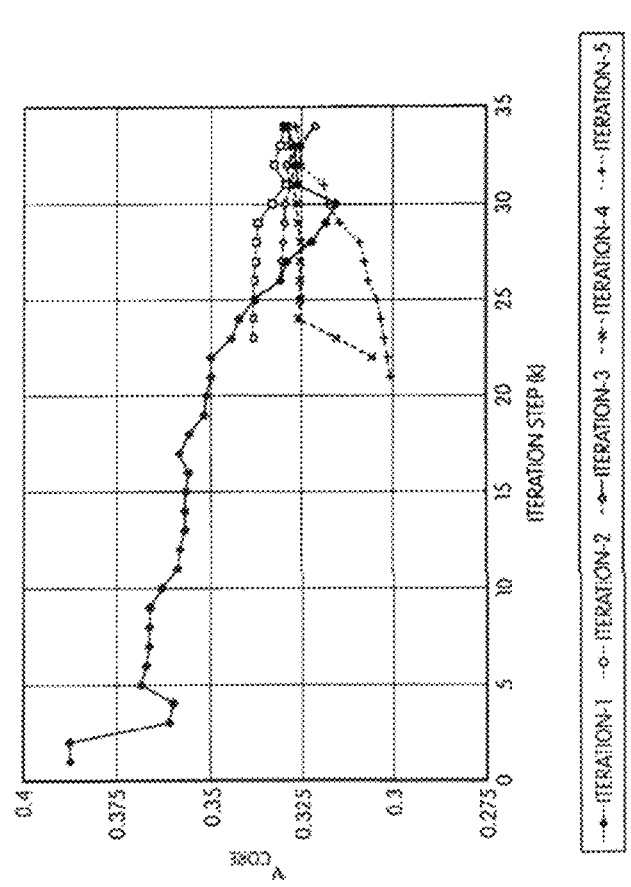
FIG. 10C illustrates the convergence of vcore (c) of the Tablet 1 during the sensitivity iterations.
Figure 10D:
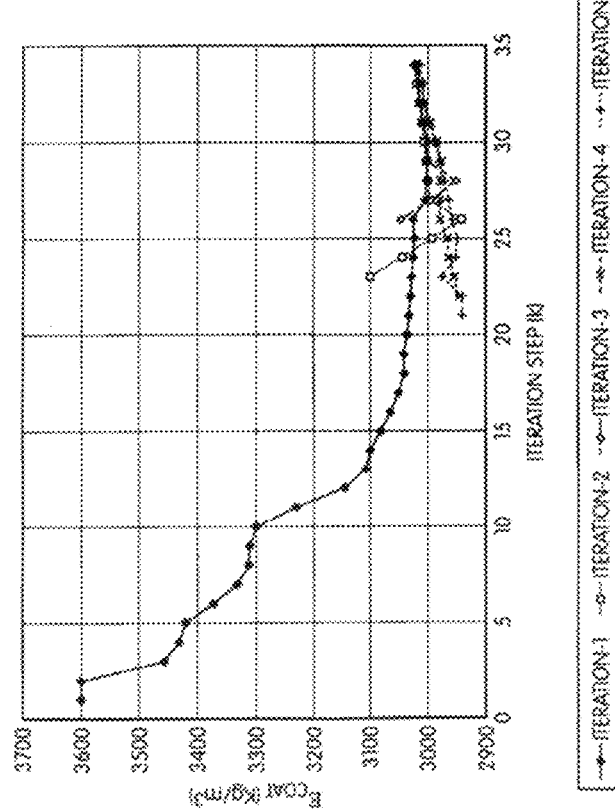
FIG. 10D illustrates the convergence of Ecoat (d) of the Tablet 1 during the sensitivity iterations.
Figure 10E:
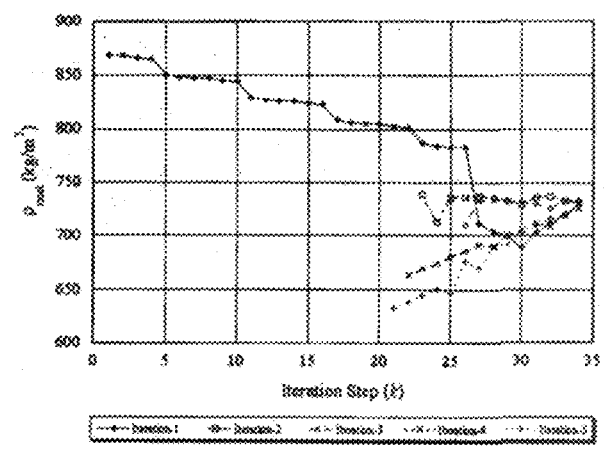
FIG. 10E illustrates the convergence of ρcoat (e) of the Table 1 during the sensitivity iterations.
Figure 10F:
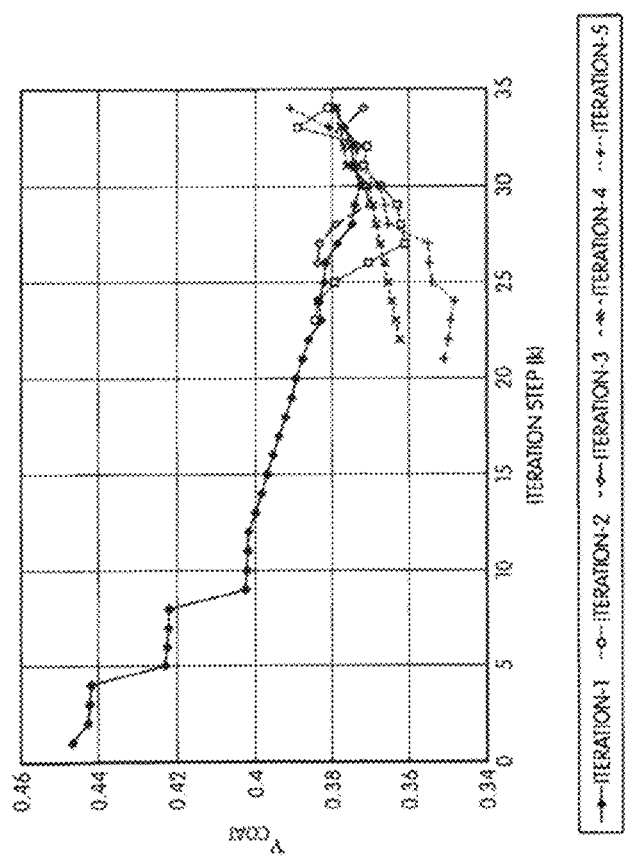
FIG. 10F illustrates the convergence of vcoat (f) of the Tablet 1 during the sensitivity iterations.

The sensitivity order of resonance frequencies regarding changes in mechanical properties from most to least sensitive are; $E_{core}, \rho_{core}, E_{coat}, \rho_{coat}, \nu_{core}$ and $\nu_{coat}$ (See FIG. 9). Convergence of the mechanical property parameters of Tablet 1 in the iterative loop is depicted in FIGS. 8A-8C. Local convergence of each mechanical property is also illustrated in FIGS. 10A-10F.

Multi-Component Tablets

Turning to FIG. 14, a picture of a vertical cross section of a sample dry coated tablet 1400 (a special form of multiand is configured/structured to deliver an acoustic pulse 1606 directed toward the dry coated tablet 1400 for the purpose of gathering data related to the dry coated tablet 1400 for the ultimate purpose of monitoring and/or characterizing the dry coated tablet 1400 as described herein. In other implementations of the system 1600, it is contemplated that a number of transducers can be mounted in the lower punch and/or the die in pulse-echo and/or pitch-catch configurations.

The transducer 1604 can be in wired or wireless communication 1608 with a vibroacoustic excitation and receiver unit 1610 (for receiving commands from or delivering acquired data to the vibroacoustic excitation and receiver unit 1610), which can be in wired or wireless communication 1608 with a digitizing oscilloscope 1612 and a computer with specialized vibroacoustic analysis software unit 1614 (which can be configured/programmed to direct the other components of the system to perform the in-die monitoring and/or characterizing of multi-component tablets in accordance with an embodiment of the present invention). Stated differently, the computer/software unit 1614 can be used for signal processing of the acquired data from the vibroacoustic excitation and receiver unit 1610 for vibroacoustic modal analysis.

The wireless communication/transmission can be over a network (not shown), which can be any suitable wired or wireless network capable of transmitting communication, including but not limited to a telephone network, Internet, Intranet, local area network, Ethernet, online communication, offline communications, wireless communications and/or similar communications means. Further, the data can be encrypted if needed based on the sensitivity of the data or the location the die/punch simulator 1602 or the computer/software unit 1614, for example. Each of the components of the vibroacoustic excitation and detection system 1600 can be located in the same room, in different rooms in the same building, and/or in a completely different building and location from each other.

Figure 17:
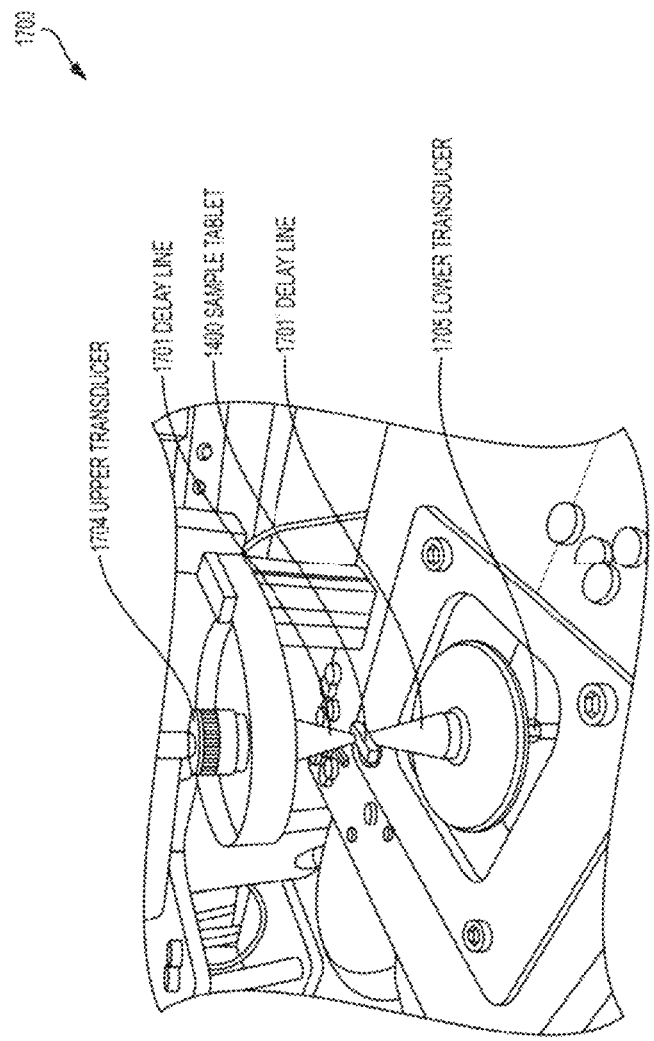
FIG. 17 is a schematic representation of a vibroacoustic excitation and detection system, which is used for out-of-die monitoring and/or characterizing multi-component tablets in accordance with an embodiment of the present invention.

FIG. 17 is a schematic representation of a vibroacoustic excitation and detection system 1700, which is used for out-of-die monitoring and/or characterizing multi-component tablets in accordance with an embodiment of the present invention. The vibroacoustic excitation and detection system 1700 can include, but is not limited to, an upper transducer 1704 connected to an upper delay line 1701, a lower transducer 1705 connected to a lower delay line 1701', and a dry coated tablet 1400 held between the upper delay line 1701 and the lower delay line 1701'. The vibroacoustic excitation and detection system 1700 can also include the other listed elements described with respect to and shown in FIG. 16 including the vibroacoustic excitation and receiver unit 1610, which can be in wired or wireless communication 1608 with the upper and/or lower transducers (1704/1705), a digitizing oscilloscope 1612, and a computer with specialized vibroacoustic analysis software unit 1614 (which can be configured/programmed to direct the other components of the system perform the out-of-die monitoring and/or characterizing of multi-component tablets in accordance with an embodiment of the present invention).

Vibrational analysis (e.g. resonance (natural) frequencies, mode shapes, etc.) in addition to wave propagation analysis (e.g. Time-of-flight, dispersion properties of waves, etc.) is performed on the data collected by each vibroacoustic excitation and detection system 1600 and 1700 with respect to the subject multi-component tablets (materials and geometries). In accordance with an embodiment of the present invention, the vibrational properties of a tablet (or multi-component tablet) solid dosage are taken advantage of. In brief, the resonance (natural) frequencies and mode shapes of a vibrating tablet (or multi-component tablet) solid dosage depends on its mechanical properties and their distribution inside the body (such as mass density, Young's modulus, Poisson's ratio, etc.) as well as geometric characteristics (e.g. shape, dimensions, layer thicknesses, geometric irregularities etc.). Consequently, in principle, these properties and characteristics can be extracted for a tablet (or multi-component tablet) and/or their sample-to-sample variations can be monitored when its resonance (natural) frequencies and mode shapes are experimentally available. Moreover, as material defects (e.g. degradation, faulty starting materials, moisture levels, etc.) and geometric irregularities (e.g. cracks, delamination, interfacial loss-of-bonding, shape and dimensions imperfections) in a tablet (or multi-component tablet) change its resonance (natural) frequencies and mode shapes, depending upon the extent of the defects and irregularities. Based on the experimental measurements of such shifts, the quality of solid dosage can be monitored, and defect states in tablets can be determined.

Various well-published generic computational techniques, as should be understood by those of skill in the art, are available to be used for the actual numerical extractions of the resonance frequencies and mode shapes of a solid body from experimental data.

Stiction and Tooling Material Modifications on Punch and Die Surfaces During Compaction Embodiments of the present invention can also include a novel non-contact method and system for detecting and monitoring stiction and tooling material modifications (such as pitting) on the surfaces and bodies of punches and dies during compaction (which can be done in real time) based on acoustic/ultrasonic waves. The monitoring/detecting can be wireless, be performed in real time, and non-invasive.

Figure 18:
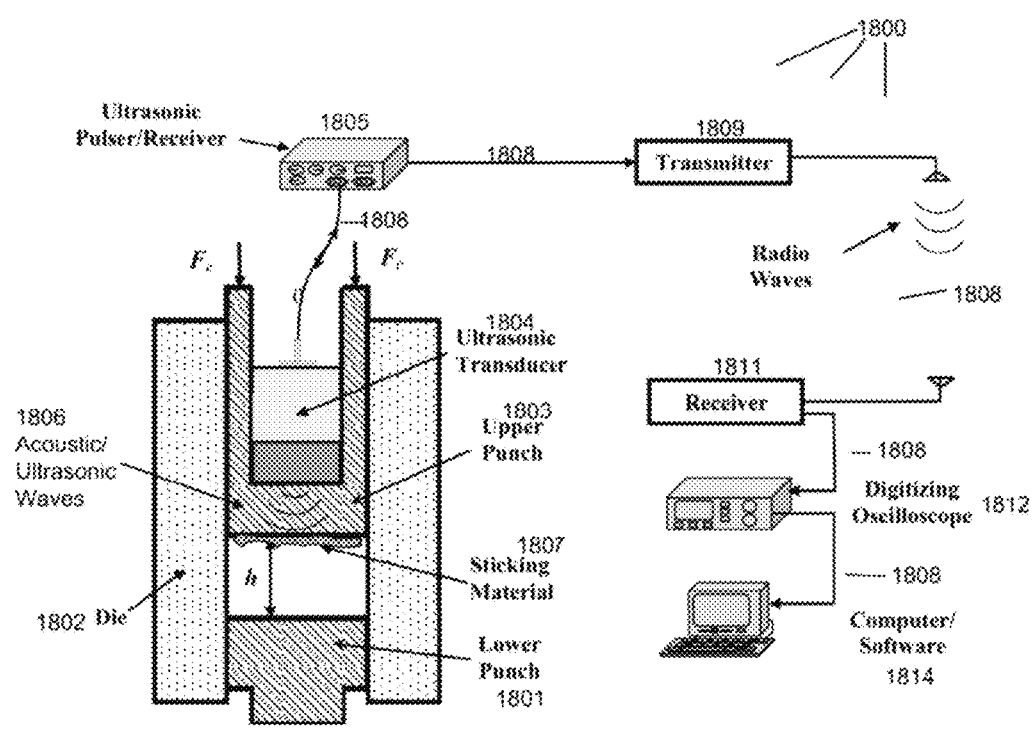
FIG. 18 is a schematic representation of a system for detecting and monitoring stiction and tooling material modifications on the surfaces and bodies of punches and dies, in accordance with an embodiment of the present invention.

FIG. 18 is a schematic representation of a system 1800 for detecting and monitoring stiction and tooling material modifications on the surfaces and bodies of punches and dies, in accordance with an embodiment of the present invention. The system 1800 can include, but is not limited to, a die 1802, a lower punch 1801, and an upper punch 1803, portions of which may include sticking material 1807. In FIG. 18, only the stiction on the upper punch 1803 is shown, but stiction on the lower punch 1801 and die 1802 can also be determined. An ultrasonic transducer 1804 is shown mounted in the upper punch. The transducer 1804, or additional transducers can be mounted elsewhere in the die or punches. For example, for the detection on the die side walls, transducers can be mounted in the die material. The transducer 1804 is configured/structured to deliver an acoustic/ultrasonic waves 1806 directed toward the surfaces and bodies of punches and dies for the purpose of gathering data for the ultimate purpose of detecting and monitoring stiction and tooling material modifications on the surfaces and bodies of punches and dies as described herein.

The transducer 1804 can be in wired or wireless communication 1808 with a ultrasonic pulser/receiver unit 1805 (for receiving commands from or delivering acquired data to the ultrasonic pulser/receiver unit 1805), which can be in wired or wireless communication 1608 with a transmitter 1809. The transmitter 1809 can be in wired or wireless communication 1608 (radio waves are shown) with a receiver 1811 to transmit the acquired data to the receiver 1811. The receiver 1811 can be in wired or wireless communication with a digitizing oscilloscope 1812, which can be in wired or wireless communication 1808 with a computer with specialized vibroacoustic analysis software unit 1814 (which can be configured/programmed to direct the other components of the system to perform the detecting and monitoring stiction and tooling material modifications on the surfaces and bodies of punches and dies in accordance with an embodiment of the present invention). The transmitter 1809 and the receiver 1811 do not need to be separate devices; they can be parts of the ultrasonic pulser/receiver 1805 and the digitizing oscilloscope respectively.

As noted elsewhere herein, the wireless communication/transmission can be over a network (not shown), which can be any suitable wired or wireless network capable of transmitting communication, including but not limited to a telephone network, Internet, Intranet, local area network, Ethernet, online communication, offline communications, wireless communications and/or similar communications means. Further, the data can be encrypted if needed based on the sensitivity of the data or the location the die 1802 or the computer/software unit 1814, for example. Each of the components of the system 1800 can be located in the same room, in different rooms in the same building, and/or in a completely different building and location from each other.

In stiction monitoring and characterization/detection in accordance with an embodiment of the present invention, the practical interest is in the modification to the surfaces while in die/punch material modification, changes in the materials properties in the material body as well as surfaces are of interest. In the disclosed system 1800, surface and body changes are detected by processing the acoustic/ultrasonic waveforms (data) generated and acquired with an embedded transducer(s) 1804. The transducer 1804 is excited by a pulser/receiver unit 1805 as shown in FIG. 18. The state of the material body and surfaces are determined by the analysis of such waveforms (see FIG. 20 for example).

In this disclosure, a system 1800 and a method are detailed for the objective of real-time monitoring of the die/punch 1802/1801/1803 sets during compaction operations. The waveforms are obtained several times during each cycle of the compaction operation, and are preferably transmitted wirelessly 1808 to a local computer 1814 for analysis and/or transmission to another user via the Internet and/or another network. See FIG. 20 for a sample waveform for a punch with no defect or modification. The analysis software 1814 that implements the disclosed method produces real-time data on the state of the die/punch 1802/1801/1803 sets on a compaction press. Such data and its processing can be used for determining various operational actions, such as process control (e.g. changes to the formulation and compaction press parameters) replacement of tools, scheduling inspections, maintenance planning, and preventive maintenance tasks.

Any of the analyses described herein, including but not limited to vibrational analysis (e.g. resonance (natural) frequencies, mode shapes, etc.) and wave propagation analysis can be performed to determine stiction and tooling material modifications on the surfaces and bodies of punches and dies, in accordance with an embodiment of the present invention.

Figure 19:
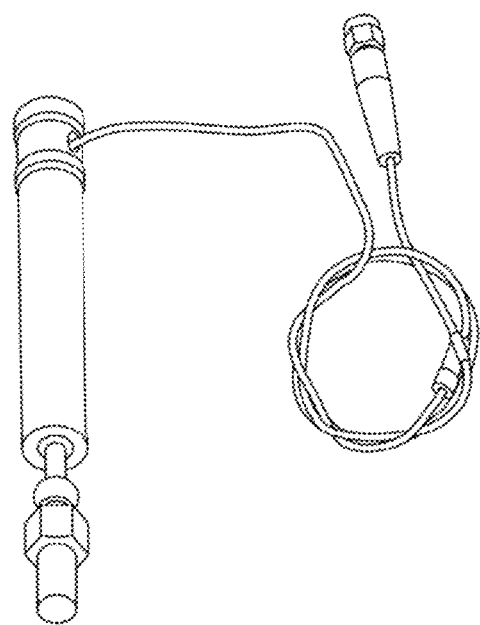
FIG. 19 is a photograph of an experimental set-up of a system for detecting and monitoring stiction and tooling material modifications on the surfaces and bodies of punches and dies with an instrumented upper punch and tooling housing apparatus, in accordance with an embodiment of the present invention.

FIG. 19 shows a photograph of an experimental set-up of system 1800 with an instrumented upper punch 1803 and tooling housing apparatus. In a preferred industrial implementation, the shown electronics can be miniaturized and integrated into punches and dies.

Figure 20:
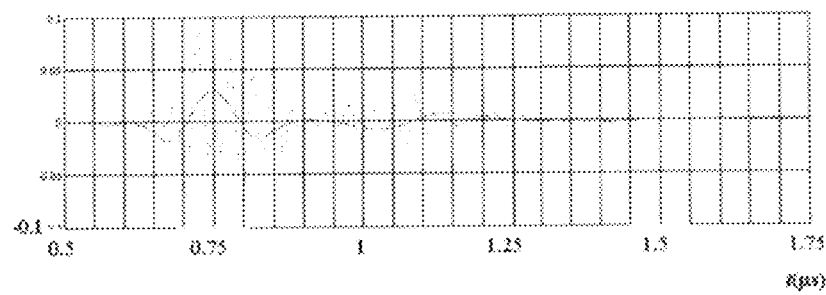
FIG. 20 is a graph showing tip-only waveforms from a wired (solid lines) and wireless (dotted lines) set-ups, demonstrating the difference between directly wired data and the noisy wireless data, in accordance with an embodiment of the present invention.

FIG. 20 is a graph showing tip-only waveforms from a wired (solid lines) and wireless (dotted lines) set-ups, demonstrating the difference between directly wired data and the noisy wireless data.

Figure 21:
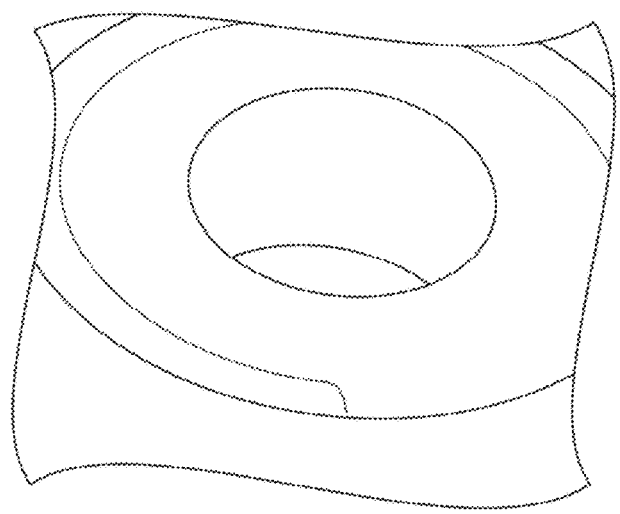
FIG. 21 is a photograph of a compactions with material deposition (modifications) in the inner walls of a die, in accordance with an embodiment of the present invention.

FIG. 21 shows a photograph of a compactions with material deposition (modifications) in the inner walls of a die.

CONCLUSIONS AND REMARKS

In the present disclosure, a non-destructive/non-contact testing platform for determining the mechanical properties of drug tablets has been described. A computational procedure for extracting mechanical property parameters from measured resonance frequencies of tablets is developed and implemented. The effectiveness of the procedure for extracting the mechanical properties (Young's modulus, Poisson's ratio and mass density) of a core and coating layer of tablets from a set of experimentally obtained resonance frequencies is demonstrated. A main conclusion is that mechanical properties can be extracted utilizing the discussed experimental methodology and the iterative computational procedure based on subsets of the resonance frequencies of the tablet. Acquired experimental resonance frequencies agree quantitatively well with the finite element-based resonance frequencies corresponding to the extracted mechanical properties. Analysis also revealed that resonance frequencies of a sample tablet are most sensitive to changes in $E_{core}$, and least sensitive to changes in $v_{coat}$.

The principal applications of the methods and apparatuses disclosed include (i) real-time quality and mechanical integrity of tablet during compaction, (ii) real-time characterization of tablet property determination during compaction, and (iii) specialized defect detection and characterization methods of drug tablets.

Figure 12B:
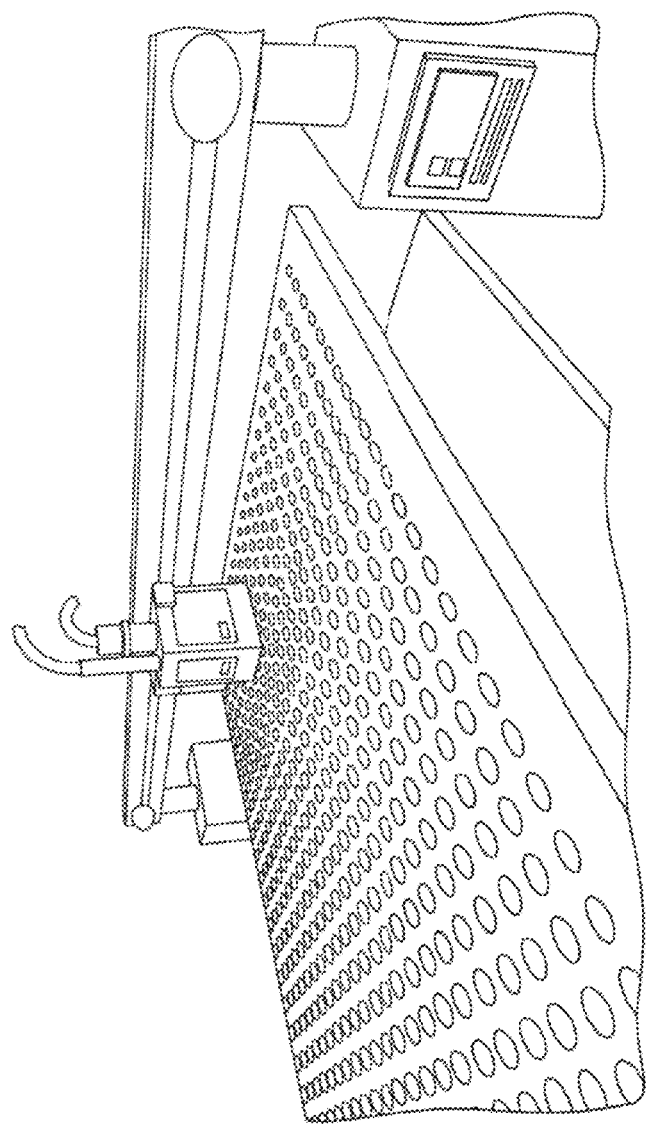
FIG. 12B illustrates an example of another potential use of the tablet monitoring evaluation platform including a desktop testing unit and an online monitoring system.
Figure 13:
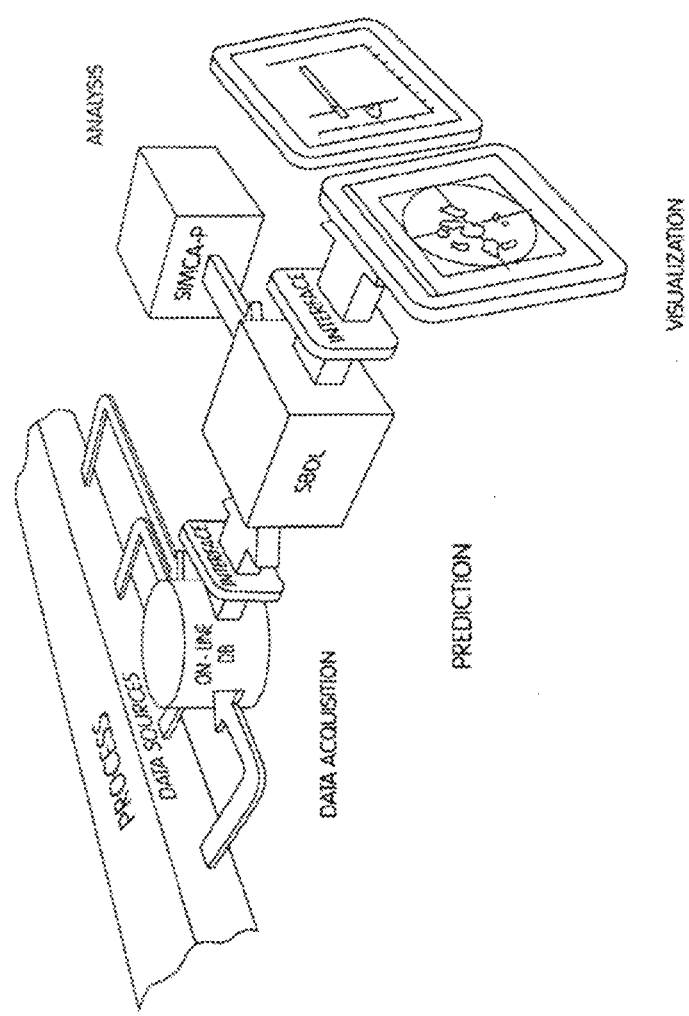
FIG. 13 illustrates a connectivity diagram of various components of a monitoring system.

FIGS. 12A-12B illustrate examples of potential uses of the tablet monitoring/evaluation platform including a design of a desktop testing unit and an online monitoring system. FIG. 13 illustrates a connectivity diagram of various components of a typical monitoring system. The functions of the tablet monitoring/evaluation platform can be integrated into an existing system.

Further, the disclosed in-die/out-of-die monitoring and/or characterizing of multi-component tablets approach is for determining the mechanical (physical), interfacial bonding and geometric (size, wall/core thicknesses, core eccentricity, and so on) quality of such multi-component products by acquiring and processing multi-component products' responses to acoustic and vibrational excitations. These mechanical (physical), interfacial, and geometric properties affect the modal structure of the tablet. In this disclosed approach, the variations in the modal response (resonance frequencies and mode shapes) are related to the mechanical (physical), interfacial, and geometric properties using analytical/computational and statistical methods, as disclosed herein. The disclosed method and system for in-die/out-of-die monitoring and/or characterizing of multi-component tablets can be adopted for inline/online monitoring and characterization of such tablet products as well as post-production quality monitoring and characterization applications when the product is still in the production and/or in the post-production phase.

The illustrative embodiments and modifications thereto described hereinabove are merely exemplary. It is understood that other modifications to the illustrative embodiments will readily occur to persons of ordinary skill in the art. All such modifications and variations are deemed to be within the scope and spirit of the present invention as will be defined by the accompanying claims.

What is claimed is:

1. A method of detecting or monitoring powder materials sticking, tooling material mechanical property changes, or tooling geometric modifications at least one punch or die surface during compaction comprising the steps of:

transmitting a first set of acoustic or ultrasonic waves onto the surfaces of said at least one punch or die surface;

receiving a second set of acoustic or ultrasonic waves from said at least one punch or die surface;

analyzing data received from said second set of acoustic or ultrasonic waves;

determining a vibration resonance frequency of said at least one punch or die surface based on said analyzed data; and determining a material accumulation level, geometric deformation level, or a material defect state of said at least one punch or die surface based on said determined vibration resonance frequency.

2. The method of claim 1, further comprising the step of obtaining acoustic or ultrasonic reflection coefficients, or acoustic or ultrasonic reflection transmission coefficients of said at least one punch or die surface.

3. The method of claim 2, wherein said step of determining further comprises the step of comparing said determined resonance frequency of said at least one punch or die surface with an original resonance frequency of said at least one punch or die surface.

4. A system for detecting or monitoring powder materials sticking, tooling material mechanical property changes, or tooling geometric modifications at least one punch or die surface during compaction comprising:
- a first transducer configured to transmit a first set of acoustic or ultrasonic waves onto the surfaces of said at least one punch or die surface and to receive a second set of acoustic waves from said at least one punch or die surface;
- a digitizing oscilloscope configured to receive and analyze second set of acoustic or ultrasonic wave data from said first transducer;
- a non-transitory computer-readable storage medium having program code for determining a vibration resonance frequency of said at least one punch or die surface based on said analyzed data, and for determining a material accumulation level, geometric deformation level, or a material defect state of said at least one punch or die surface based on said determined vibration resonance frequency or a measured surface reflection and transmission coefficients.

5. The system of claim 4, wherein said non-transitory computer-readable storage medium further has program code for comparing said determined resonance frequency or the measured surface reflection and transmission coefficients of said at least one punch or die surface with an original resonance frequency of said at least one punch or die surface.

* * * * *